United States Patent
Trotter et al.

(10) Patent No.: US 11,002,658 B2
(45) Date of Patent: May 11, 2021

(54) CHARACTERIZATION AND SORTING FOR PARTICLE ANALYZERS

(71) Applicant: BECTON, DICKINSON AND COMPANY, Franklin Lakes, NJ (US)

(72) Inventors: Joseph Trotter, La Jolla, CA (US); Paul Barclay Purcell, Ouray, CO (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 193 days.

(21) Appl. No.: 16/390,754

(22) Filed: Apr. 22, 2019

(65) Prior Publication Data

US 2019/0331586 A1    Oct. 31, 2019

Related U.S. Application Data

(60) Provisional application No. 62/663,106, filed on Apr. 26, 2018.

(51) Int. Cl.
*G01N 15/14* (2006.01)
*B07C 5/342* (2006.01)
*G01N 15/10* (2006.01)

(52) U.S. Cl.
CPC ....... *G01N 15/1429* (2013.01); *B07C 5/3425* (2013.01); *G01N 15/1425* (2013.01); *G01N 2015/1006* (2013.01); *G01N 2015/1081* (2013.01)

(58) Field of Classification Search
CPC combination set(s) only.
See application file for complete search history.

(56) References Cited

U.S. PATENT DOCUMENTS

| | | |
|---|---|---|
| 5,627,040 A | 5/1997 | Bierre et al. |
| 2008/0172185 A1 | 7/2008 | Yi et al. |
| 2011/0010144 A1 | 1/2011 | Fox et al. |
| (Continued) | | |

FOREIGN PATENT DOCUMENTS

KR    1020170128786    11/2017

OTHER PUBLICATIONS

Pyne, et al. "Automated high-dimensional flow cytometric data analysis", PNAS, May 26, 2009, vol. 106, No. 21, 8519-8524.

*Primary Examiner* — Terrell H Matthews
(74) *Attorney, Agent, or Firm* — Bret E. Field; Bozicevic, Field & Francis LLP

(57) ABSTRACT

Some embodiments of the methods provided herein relate to sample analysis and particle characterization methods. Some such embodiments include receiving, from a particle analyzer, measurements for a first portion of particles associated with an experiment. Some embodiments also include generating a tree representing groups of related particles based at least in part on the measurements, wherein the tree includes at least three groups. Some embodiments also include generating a measure of relatedness between a first group and a second group of the tree based at least in part on the measurements. Some embodiments also include and configuring the particle analyzer to classify a subsequent particle associated with the experiment with the first group real-time, wherein the subsequent particle is not included in the first portion of particles. Some embodiments also include sorting the subsequent particle.

20 Claims, 9 Drawing Sheets

(56) References Cited

U.S. PATENT DOCUMENTS

| | | | |
|---|---|---|---|
| 2014/0172772 A1* | 6/2014 | Sanchez Loureda | G06N 7/005 706/52 |
| 2015/0253247 A1* | 9/2015 | Nitta | G01N 15/1459 435/288.7 |
| 2016/0169786 A1 | 6/2016 | Albitar et al. | |
| 2018/0137192 A1* | 5/2018 | Zaribafiyan | G06F 16/285 |
| 2019/0026926 A1* | 1/2019 | Crespo-Diaz | G01N 15/1429 |
| 2019/0331586 A1* | 10/2019 | Trotter | G01N 15/1429 |

* cited by examiner

CHARACTERIZATION AND SORTING FOR PARTICLE ANALYZERS

CROSS-REFERENCE TO RELATED APPLICATION

Pursuant to 35 U.S.C. § 119(e), this application claims priority to the filing date of U.S. Provisional Patent Application Ser. No. 62/663,106 filed Apr. 26, 2018; the disclosure of which application is incorporated herein by reference.

FIELD

This disclosure relates to relates generally to the field of automated particle assessment, and more particularly to sample analysis and particle characterization methods.

INTRODUCTION

Particle analyzers, such as flow and scanning cytometers, are analytical tools that enable the characterization of particles on the basis of electro-optical measurements such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of photodetectors, one for each of the scatter parameters to be measured, and one or more for each of the distinct dyes to be detected are included in the analyzer. For example, some embodiments include spectral configurations where more than one sensor or detector is used per dye. The data obtained comprise the signals measured for each of the light scatter detectors and the fluorescence emissions.

Particle analyzers may further comprise means for recording the measured data and analyzing the data. For example, data storage and analysis may be carried out using a computer connected to the detection electronics. For example, the data can be stored in tabular form, where each row corresponds to data for one particle, and the columns correspond to each of the measured features. The use of standard file formats, such as an "FCS" file format, for storing data from a particle analyzer facilitates analyzing data using separate programs and/or machines. Using current analysis methods, the data typically are displayed in 1-dimensional histograms or 2-dimensional (2D) plots for ease of visualization, but other methods may be used to visualize multidimensional data.

The parameters measured using, for example, a flow cytometer typically include light at the excitation wavelength scattered by the particle in a narrow angle along a mostly forward direction, referred to as forward scatter (FSC), the excitation light that is scattered by the particle in an orthogonal direction to the excitation laser, referred to as side scatter (SSC), and the light emitted from fluorescent molecules in one or more detectors that measure signal over a range of spectral wavelengths, or by the fluorescent dye that is primarily detected in that specific detector or array of detectors. Different cell types can be identified by their light scatter characteristics and fluorescence emissions resulting from labeling various cell proteins or other constituents with fluorescent dye-labeled antibodies or other fluorescent probes.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1994); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

The data obtained from an analysis of cells (or other particles) by multi-color flow cytometry are multidimensional, wherein each cell corresponds to a point in a multi-dimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots," of the data. Alternatively, clusters can be identified, and gates that define the limits of the populations, can be determined automatically. Examples of methods for automated gating have been described in, for example, U.S. Pat. Nos. 4,845,653; 5,627,040; 5,739,000; 5,795,727; 5,962,238; 6,014,904; and 6,944,338; and U.S. Pat. Pub. No. 2012/0245889, each incorporated herein by reference.

Flow cytometry is a valuable method for the analysis and isolation of biological particles such as cells and constituent molecules. As such it has a wide range of diagnostic and therapeutic applications. The method utilizes a fluid stream to linearly segregate particles such that they can pass, single file, through a detection apparatus. Individual cells can be distinguished according to their location in the fluid stream and the presence of detectable markers. Thus, a flow cytometer can be used to characterize and produce a diagnostic profile of a population of biological particles.

Isolation of biological particles has been achieved by adding a sorting or collection capability to flow cytometers. Particles in a segregated stream, detected as having one or more desired characteristics, are individually isolated from the sample stream by mechanical or electrical separation. This method of flow sorting has been used to sort cells of different types, to separate sperm bearing X and Y chromosomes for animal breeding, to sort chromosomes for genetic analysis, and to isolate particular organisms from complex biological population.

Gating is used to classify and help make sense of the large quantity of data that may be generated from a sample. Given the large quantities of data presented for a given sample, there exists a need to efficiently control the graphical display of the data.

Fluorescence-activated particle sorting or cell sorting is a specialized type of flow cytometry. It provides a method for sorting a heterogeneous mixture of particles into one or more containers, one cell at a time, based upon the specific light scattering and fluorescent characteristics of each cell. It records fluorescent signals from individual cells, and physically separates cells of particular interest. The acronym FACS is trademarked and owned by Becton Dickinson and may be used to refer to devices for performing fluorescence-activated particle sorting or cell sorting.

The particle suspension is placed near the center of a narrow, rapidly flowing stream of liquid. The flow is arranged so that on the average there is a large separation between particles relative to their diameter as they arrive stochastically (Poisson process) into the detection region. A vibrating mechanism causes the emerging fluid stream to break off in a stable manner into individual droplets that contain particles previously characterized in the detection region. The system is generally adjusted so that there is a low probability of more than one particle being in a droplet. If a particle is classified to be collected, a charge is applied to the flow cell and emerging stream during the period of time one or more drops form and break off from the stream. These charged droplets then move through an electrostatic deflection system that diverts droplets into target containers based upon the charge applied to the droplet.

A sample can include thousands if not millions of cells. Cells may be sorted to purify a sample to the cells of interest. The sorting process can generally identify three varieties of cells: cells of interest, cells which are not of interest, and cells which cannot be identified. In order to sort cells with high purity (e.g., high concentration of cells of interest), droplet generating cell sorters typically abort the sort electronically if the desired cells are too close to another unwanted cell and thereby reduce contamination of the sorted populations by any inadvertent inclusion of an unwanted particle within the droplet containing the particle of interest.

SUMMARY

Some embodiments include a computer-implemented method that includes the following: under control of one or more processing devices, receiving, from a particle analyzer, measurements for a first portion of particles associated with an experiment; generating a tree representing groups of related particles based at least in part on the measurements, wherein the tree includes at least three groups; generating a measure of relatedness between a first group and a second group of the tree based at least in part on the measurements; and configuring the particle analyzer to classify a subsequent particle associated with the experiment with the first group, wherein the subsequent particle is not included in the first portion of particles.

Some embodiments of the method further include receiving gate information identifying a range of measurements for classifying the subsequent particle, wherein the first group is defined by the gate information.

Some embodiments of the method include unsupervised learning, wherein the first group is defined by the gate information. In some embodiments, the method includes receiving gate information identifying a range of measurements for classifying the subsequent particle, wherein the first group is defined by the gate information; determining that a difference between a result of the unsupervised learning, and the gate information, corresponds to a threshold; and causing display of an alert identifying the difference.

In some embodiments, the method includes generating the measure of relatedness between the first group and the second group based at least in part on a probability density function to characterize event distances between events included in the first group and the second group. In some embodiments, the probability density function includes a Euclidean distance function. In some embodiments, the probability density function comprises a Mahalanobis distance function. Some embodiments of the method include receiving an inclusion threshold for the first group, wherein the inclusion threshold identifies a first range of measurements for including an unclassified particle in the first group relative to the first group; and receiving an exclusion threshold for the first group, wherein the exclusion threshold identifies a second range of measurements for excluding the unclassified particle from the first group relative to the second group; wherein the subsequent particle is classified with the first group based at least in part on the inclusion threshold and the exclusion threshold.

Some embodiments of the method include generating a covariance matrix based at least in part on a likelihood of an association between the subsequent particle and each of the first group and the second group; wherein configuring the particle analyzer includes adjusting a sorting circuit included in the particle analyzer based at least in part on the covariance matrix. In some embodiments, the sorting circuit is a field programmable gate array.

In some embodiments, the measurements received from the particle analyzer include measurements of light emitted fluorescently by the first portion of particles. In some embodiments, the light emitted fluorescently by the first portion of particles includes light emitted fluorescently by antibodies bound to the first portion of particles.

In some embodiments, generating the measure of relatedness is performed only for the first and second groups of the tree. Some embodiments include directing the subsequent particle to a collection vessel.

Some embodiments include a system that includes: one or more processing devices; and a computer-readable storage medium that includes instructions that, when executed by the one or more processing devices, causes the system to, receive, from a particle analyzer, measurements for a first portion of particles associated with an experiment; generate a tree representing groups of related particles based at least in part on the measurements, wherein the tree includes at least three groups; generate a measure of relatedness between a first group and a second group of the tree based at least in part on the measurements; and configure the particle analyzer to classify a subsequent particle associated with the experiment with the first group, wherein the subsequent particle is not included in the first portion of particles.

Some embodiments include a method of computational configuration of a particle analyzer according to any of the embodiments disclosed herein. Some embodiments include a computer-readable medium having stored thereon instructions which when executed perform any of the methods disclosed herein. Some embodiments include an apparatus that includes a processor, wherein the processor is configured to perform any of the methods disclosed herein.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
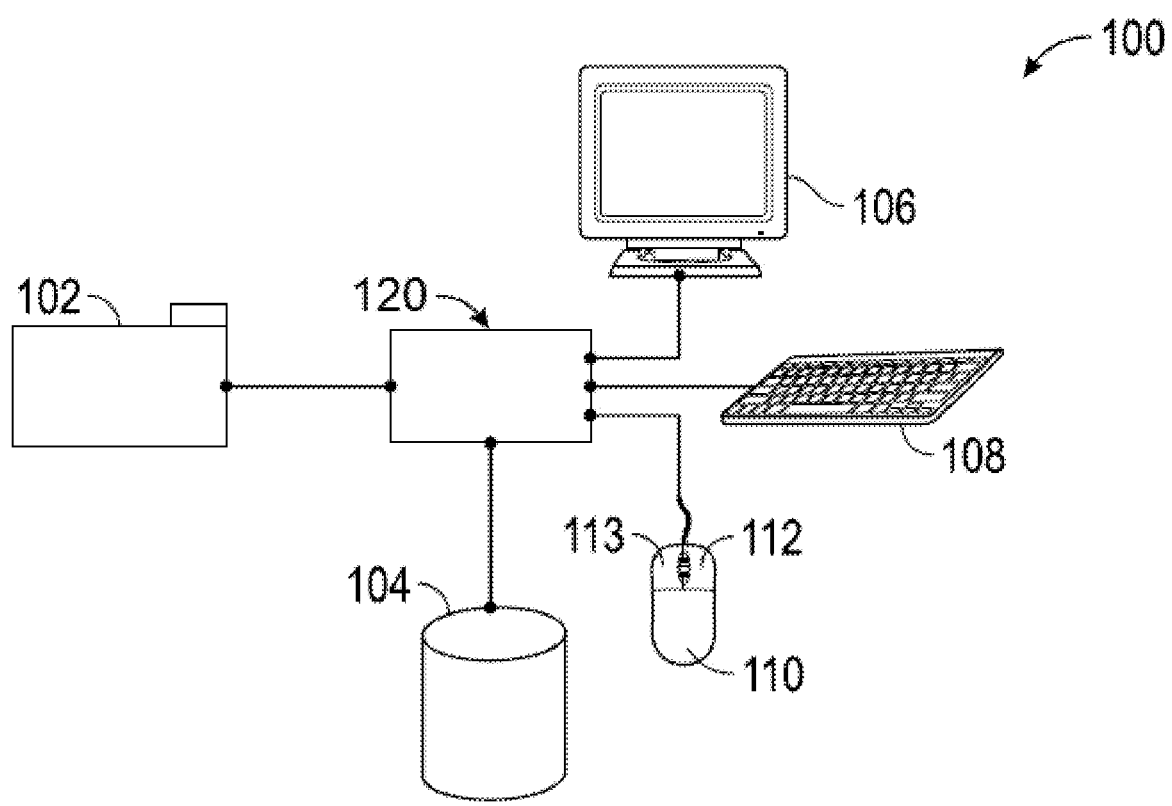
FIG. 1 shows a functional block diagram for one example of a graphics control system for analyzing and displaying biological events.

Some embodiments of the methods provided herein relate to sample analysis and particle characterization methods. Some such embodiments include receiving, from a particle analyzer, measurements for a first portion of particles associated with an experiment; generating a tree representing groups of related particles based at least in part on the measurements and features characterized, wherein the tree includes at least three groups; generating a measure of relatedness between a first group and a second group of the tree based at least in part on the measurements; and configuring the particle analyzer to classify a subsequent particle associated with the experiment with the first group, wherein the subsequent particle is not included in the first portion of particles. Some embodiments also include sorting the subsequent particle such as by directing the subsequent particle to a specified collection location (e.g., well or collection tube).

As used herein, the terms set forth with particularity below have the following definitions. If not otherwise defined in this section, all terms used herein have the meaning commonly understood by a person skilled in the arts to which this invention belongs.

As used herein, "system," "instrument," "apparatus," and "device" generally encompass both the hardware (e.g., mechanical and electronic) and, in some implementations, associated software (e.g., specialized computer programs for graphics control) components.

As used herein, an "event" generally refers to the packet of data measured from a single particle, such as cells or synthetic particles. Typically, the data measured from a single particle include a number of parameters, including one or more light scattering parameters, and at least one parameter or feature derived from fluorescence detected from the particle such as the intensity of the fluorescence. Thus, each event is represented as a vector of measurements and features, wherein each measured parameter or feature corresponds to one dimension of the data space. In some embodiments, the data measured from a single particle include image, electric, temporal, or acoustic data.

As used herein, a "population", or "subpopulation" of particles, such as cells or other particles, generally refers to a group of particles that possess properties (for example, optical, impedance, or temporal properties) with respect to one or more measured parameters such that measured parameter data form a cluster in the data space. Thus, populations are recognized as clusters in the data. Conversely, each data cluster generally is interpreted as corresponding to a population of a particular type of cell or particle, although clusters that correspond to noise or background typically also are observed. A cluster may be defined in a subset of the dimensions, e.g., with respect to a subset of the measured parameters, which corresponds to populations that differ in only a subset of the measured parameters or features extracted from the measurements of the cell or particle.

As used herein, a "gate" generally refers to a classifier boundary identifying a subset of data of interest. In cytometry, a gate may bound a group of events of particular interest. As used herein, "gating" generally refers to the process of classifying the data using a defined gate for a given set of data, where the gate may be one or more regions of interest combined with Boolean logic. As used herein, an "event" generally refers to the assembled packet of data measured from a single particle, such as cells or synthetic particles). Typically, the data measured from a single particle include a number of parameters or features, including one or more light scattering parameters or features, and at least one other parameter or feature derived from measured fluorescence. Thus, each event is represented as a vector of parameter and feature measurements, wherein each measured parameter or feature corresponds to one dimension of the data space.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.
Systems for Characterizing Particles of a Sample As summarized above, aspects of the present disclosure include systems for characterizing particles of a sample. Systems according to certain embodiments include: one or more processing devices; and a computer-readable storage medium that includes instructions that, when executed by the one or more processing devices, causes the system to, receive, from a particle analyzer, measurements for a first portion of particles associated with an experiment; generate a tree representing groups of related particles based at least in part on the measurements, wherein the tree includes at least three groups; generate a measure of relatedness between a first group and a second group of the tree based at least in part on the measurements; and configure the particle analyzer to classify a subsequent particle associated with the experiment with the first group, wherein the subsequent particle is not included in the first portion of particles.

Particle analyzer systems of interest include a light source configured to irradiate a sample having particles (e.g., cells) in a flow stream. In embodiments, the light source may be any suitable broadband or narrow band source of light. Depending on the components in the sample (e.g., cells, beads, non-cellular particles, etc.), the light source may be configured to emit wavelengths of light that vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm.

In some embodiments, the light source is a laser. Lasers of interest may include pulsed lasers or continuous wave lasers. For example, the laser may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof; a dye laser, such as a stilbene, coumarin or rhodamine laser; a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof; a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium203 laser or cerium doped lasers and combinations thereof; a semiconductor diode laser, optically pumped semiconductor laser (OPSL), or a frequency doubled- or frequency tripled implementation of any of the above mentioned lasers.

In other embodiments, the light source is a non-laser light source, such as a lamp, including but not limited to a halogen lamp, deuterium arc lamp, xenon arc lamp, a light-emitting diode, such as a broadband LED with continuous spectrum, superluminescent emitting diode, semiconductor light emitting diode, wide spectrum LED white light source, an multi-LED integrated. In some instances the non-laser light source is a stabilized fiber-coupled broadband light source, white light source, among other light sources or any combination thereof. In certain embodiments, the light source is a light beam generator that is configured to generate two or more beams of frequency shifted light. In some instances, the light beam generator includes a laser, a radiofrequency generator configured to apply radiofrequency drive signals to an acousto-optic device to generate two or more angularly deflected laser beams. In these embodiments, the laser may be a pulsed lasers or continuous wave laser. For example lasers in light beam generators of interest may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof; a dye laser, such as a stilbene, coumarin or rhodamine laser; a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof; a solid-state laser, such as a ruby laser, an Nd:YAG laser, NdCrYAG laser, Er:YAG laser, Nd:YLF laser, Nd:YVO4 laser, Nd:YCa4O(BO3)3 laser, Nd:YCOB laser, titanium sapphire laser, thulim YAG laser, ytterbium YAG laser, ytterbium203 laser or cerium doped lasers and combinations thereof.

The acousto-optic device may be any convenient acousto-optic protocol configured to frequency shift laser light using applied acoustic waves. In certain embodiments, the acousto-optic device is an acousto-optic deflector. The acousto-optic device in the subject system is configured to generate angularly deflected laser beams from the light from the laser and the applied radiofrequency drive signals. The radiofrequency drive signals may be applied to the acousto-optic device with any suitable radiofrequency drive signal source, such as a direct digital synthesizer (DDS), arbitrary waveform generator (AWG), or electrical pulse generator.

In embodiments, a controller is configured to apply radiofrequency drive signals to the acousto-optic device to produce the desired number of angularly deflected laser beams in the output laser beam, such as being configured to apply 3 or more radiofrequency drive signals, such as 4 or more radiofrequency drive signals, such as 5 or more radiofrequency drive signals, such as 6 or more radiofrequency drive signals, such as 7 or more radiofrequency drive signals, such as 8 or more radiofrequency drive signals, such as 9 or more radiofrequency drive signals, such as 10 or more radiofrequency drive signals, such as 15 or more radiofrequency drive signals, such as 25 or more radiofrequency drive signals, such as 50 or more radiofrequency drive signals and including being configured to apply 100 or more radiofrequency drive signals.

In some instances, to produce an intensity profile of the angularly deflected laser beams in the output laser beam, the controller is configured to apply radiofrequency drive signals having an amplitude that varies such as from about 0.001 V to about 500 V, such as from about 0.005 V to about 400 V, such as from about 0.01 V to about 300 V, such as from about 0.05 V to about 200 V, such as from about 0.1 V to about 100 V, such as from about 0.5 V to about 75 V, such as from about 1 V to 50 V, such as from about 2 V to 40 V, such as from 3 V to about 30 V and including from about 5 V to about 25 V. Each applied radiofrequency drive signal has, in some embodiments, a frequency of from about 0.001 MHz to about 500 MHz, such as from about 0.005 MHz to about 400 MHz, such as from about 0.01 MHz to about 300 MHz, such as from about 0.05 MHz to about 200 MHz, such as from about 0.1 MHz to about 100 MHz, such as from about 0.5 MHz to about 90 MHz, such as from about 1 MHz to about 75 MHz, such as from about 2 MHz to about 70 MHz, such as from about 3 MHz to about 65 MHz, such as from about 4 MHz to about 60 MHz and including from about 5 MHz to about 50 MHz.

In certain embodiments, the controller has a processor having memory operably coupled to the processor such that the memory includes instructions stored thereon, which when executed by the processor, cause the processor to produce an output laser beam with angularly deflected laser beams having a desired intensity profile. For example, the memory may include instructions to produce two or more angularly deflected laser beams with the same intensities, such as 3 or more, such as 4 or more, such as 5 or more, such as 10 or more, such as 25 or more, such as 50 or more and including memory may include instructions to produce 100 or more angularly deflected laser beams with the same intensities. In other embodiments, the may include instructions to produce two or more angularly deflected laser beams with different intensities, such as 3 or more, such as 4 or more, such as 5 or more, such as 10 or more, such as 25 or more, such as 50 or more and including memory may include instructions to produce 100 or more angularly deflected laser beams with different intensities.

In certain embodiments, the controller has a processor having memory operably coupled to the processor such that the memory includes instructions stored thereon, which when executed by the processor, cause the processor to produce an output laser beam having increasing intensity from the edges to the center of the output laser beam along the horizontal axis. In these instances, the intensity of the angularly deflected laser beam at the center of the output beam may range from 0.1% to about 99% of the intensity of the angularly deflected laser beams at the edge of the output laser beam along the horizontal axis, such as from 0.5% to about 95%, such as from 1%) to about 90%, such as from about 2% to about 85%, such as from about 3% to about 80%, such as from about 4% to about 75%, such as from about 5% to about 70%, such as from about 6% to about 65%, such as from about 7% to about 60%, such as from about 8% to about 55% and including from about 10% to about 50% of the intensity of the angularly deflected laser beams at the edge of the output laser beam along the horizontal axis. In other embodiments, the controller has a processor having memory operably coupled to the processor such that the memory includes instructions stored thereon, which when executed by the processor, cause the processor to produce an output laser beam having an increasing intensity from the edges to the center of the output laser beam along the horizontal axis. In these instances, the intensity of the angularly deflected laser beam at the edges of the output beam may range from 0.1% to about 99% of the intensity of the angularly deflected laser beams at the center of the output laser beam along the horizontal axis, such as from 0.5% to about 95%, such as from 1% to about 90%, such as from about 2% to about 85%, such as from about 3% to about 80%, such as from about 4% to about 75%, such as from about 5% to about 70%, such as from about 6% to about 65%, such as from about 7% to about 60%, such as from about 8% to about 55% and including from about 10% to about 50% of the intensity of the angularly deflected laser beams at the center of the output laser beam along the horizontal axis. In yet other embodiments, the controller has a processor having memory operably coupled to the processor such that the memory includes instructions stored thereon, which when executed by the processor, cause the processor to produce an output laser beam having an intensity profile with a Gaussian distribution along the horizontal axis. In still other embodiments, the controller has a processor having memory operably coupled to the processor such that the memory includes instructions stored thereon, which when executed by the processor, cause the processor to produce an output laser beam having a top hat intensity profile along the horizontal axis.

In embodiments, light beam generators of interest may be configured to produce angularly deflected laser beams in the output laser beam that are spatially separated. Depending on the applied radiofrequency drive signals and desired irradiation profile of the output laser beam, the angularly deflected laser beams may be separated by 0.001 µm or more, such as by 0.005 µm or more, such as by 0.01 µm or more, such as by 0.05 µm or more, such as by 0.1 µm or more, such as by 0.5 µm or more, such as by 1 µm or more, such as by 5 µm or more, such as by 10 µm or more, such as by 100 µm or more, such as by 500 µm or more, such as by 1000 µm or more and including by 5000 µm or more. In some embodiments, systems are configured to produce angularly deflected laser beams in the output laser beam that overlap, such as with an adjacent angularly deflected laser beam along a horizontal axis of the output laser beam. The overlap between adjacent angularly deflected laser beams (such as overlap of beam spots) may be an overlap of 0.001 µm or more, such as an overlap of 0.005 µm or more, such as an overlap of 0.01 µm or more, such as an overlap of 0.05 µm or more, such as an overlap of 0.1 µm or more, such as an overlap of 0.5 µm or more, such as an overlap of 1 µm or more, such as an overlap of 5 µm or more, such as an overlap of 10 µm or more and including an overlap of 100 µm or more.

In certain instances, light beam generators configured to generate two or more beams of frequency shifted light include laser excitation modules as described in U.S. Pat. Nos. 9,423,353; 9,784,661 and 10,006,852 and U.S. Patent Publication Nos. 2017/0133857 and 2017/0350803, the disclosures of which are herein incorporated by reference.

In embodiments, systems include a light detection system having one or more photodetectors for detecting and measuring light from the sample. Photodetectors of interest may be configured to measure light absorption (e.g., for brightfield light data), light scatter (e.g., forward or side scatter light data), light emission (e.g., fluorescence light data) from the sample or a combination thereof. Photodetectors of interest may include, but are not limited to optical sensors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, light from a sample is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors.

In some embodiments, light detection systems of interest include a plurality of photodetectors. In some instances, the light detection system includes a plurality of solid-state detectors such as photodiodes. In certain instances, the light detection system includes a photodetector array, such as an array of photodiodes. In these embodiments, the photodetector array may include 4 or more photodetectors, such as 10 or more photodetectors, such as 25 or more photodetectors, such as 50 or more photodetectors, such as 100 or more photodetectors, such as 250 or more photodetectors, such as 500 or more photodetectors, such as 750 or more photodetectors and including 1000 or more photodetectors. For example, the detector may be a photodiode array having 4 or more photodiodes, such as 10 or more photodiodes, such as 25 or more photodiodes, such as 50 or more photodiodes, such as 100 or more photodiodes, such as 250 or more photodiodes, such as 500 or more photodiodes, such as 750 or more photodiodes and including 1000 or more photodiodes.

The photodetectors may be arranged in any geometric configuration as desired, where arrangements of interest include, but are not limited to a square configuration, rectangular configuration, trapezoidal configuration, triangular configuration, hexagonal configuration, heptagonal configuration, octagonal configuration, nonagonal configuration, decagonal configuration, dodecagonal configuration, circular configuration, oval configuration as well as irregular patterned configurations. The photodetectors in the photodetector array may be oriented with respect to the other (as referenced in an X-Z plane) at an angle ranging from 10° to 180°, such as from 15° to 170°, such as from 20° to 160°, such as from 25° to 150°, such as from 30° to 120° and including from 45° to 90°.

The photodetector array may be any suitable shape and may be a rectilinear shape, e.g., squares, rectangles, trapezoids, triangles, hexagons, etc., curvilinear shapes, e.g., circles, ovals, as well as irregular shapes, e.g., a parabolic bottom portion coupled to a planar top portion. In certain embodiments, the photodetector array has a rectangular-shaped active surface.

Each photodetector (e.g., photodiode) in the array may have an active surface with a width that ranges from 5 µm to 250 µm, such as from 10 µm to 225 µm, such as from 15 µm to 200 µm, such as from 20 µm to 175 µm, such as from 25 µm to 150 µm, such as from 30 µm to 125 µm and including from 50 µm to 100 µm and a length that ranges from 5 µm to 250 µm, such as from 10 µm to 225 µm, such as from 15 µm to 200 µm, such as from 20 µm to 175 µm, such as from 25 µm to 150 µm, such as from 30 µm to 125 µm and including from 50 µm to 100 µm, where the surface area of each photodetector (e.g., photodiode) in the array ranges from 25 to µm$^2$ to 10000 µm$^2$, such as from 50 to µm$^2$ to 9000 µm$^2$, such as from 75 to µm$^2$ to 8000 µm$^2$, such as from 100 to µm$^2$ to 7000 µm$^2$, such as from 150 to µm$^2$ to 6000 µm$^2$ and including from 200 to µm$^2$ to 5000 µm$^2$.

The size of the photodetector array may vary depending on the amount and intensity of the light, the number of photodetectors and the desired sensitivity and may have a length that ranges from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm. The width of the photodetector array may also vary, ranging from 0.01 mm to 100 mm, such as from 0.05 mm to 90 mm, such as from 0.1 mm to 80 mm, such as from 0.5 mm to 70 mm, such as from 1 mm to 60 mm, such as from 2 mm to 50 mm, such as from 3 mm to 40 mm, such as from 4 mm to 30 mm and including from 5 mm to 25 mm. As such, the active surface of the photodetector array may range from 0.1 mm$^2$ to 10000 mm$^2$, such as from 0.5 mm$^2$ to 5000 mm$^2$, such as from 1 mm$^2$ to 1000 mm$^2$, such as from 5 mm$^2$ to 500 mm$^2$, and including from 10 mm$^2$ to 100 mm$^2$.

Photodetectors of interest are configured to measure collected light at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths.

In some embodiments, photodetectors are configured to measure collected light over a range of wavelengths (e.g., 200 nm-1000 nm). In certain embodiments, photodetectors of interest are configured to collect spectra of light over a range of wavelengths. For example, systems may include one or more detectors configured to collect spectra of light over one or more of the wavelength ranges of 200 nm-1000 nm. In yet other embodiments, detectors of interest are configured to measure light from the sample in the flow stream at one or more specific wavelengths. For example, systems may include one or more detectors configured to measure light at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof.

The light detection system is configured to measure light continuously or in discrete intervals. In some instances, photodetectors of interest are configured to take measurements of the collected light continuously. In other instances, the light detection system is configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

FIG. 1 shows a functional block diagram for one example of a graphics control system for analyzing and displaying biological events. A graphics controller 120 may be configured to implement a variety of processes for controlling graphic display of biological events.

A particle analyzer 102 may be configured to acquire biological event data. For example, a flow cytometer may generate flow cytometric event data. The particle analyzer 102 may be configured to provide biological event data to the graphics controller 120. A data communication channel may be included between the particle analyzer 102 and the graphics controller 120. The biological event data may be provided to the graphics controller 120 via the data communication channel.

The graphics controller 120 may be configured to receive biological event data from the particle analyzer 102. The biological event data received from the particle analyzer 102 may include flow cytometric event data. The graphics controller 120 may be configured to provide a graphical display including a first plot of biological event data to a display device 106. The graphics controller 120 may be further configured to render a region of interest as a gate around a population of biological event data shown by the display device 106, overlaid upon the first plot. In some embodiments, the gate may be a logical combination of one or more graphical regions of interest drawn upon a single parameter histogram or bivariate plot. Additionally, the graphics controller 120 may be further configured to display the biological event data on the display device 106 within the gate differently from other events in the biological event data outside of the gate. For example, the graphics controller 120 may be configured to render the color of biological event data contained within the gate to be distinct from the color of biological event data outside of the gate. The display device 106 may be implemented as a monitor, a tablet computer, a smartphone, or other electronic device configured to present graphical interfaces.

The graphics controller 120 may be configured to receive a gate selection signal identifying the gate from a first input device. For example, the first input device may be implemented as a mouse 110. The mouse 110 may initiate a gate selection signal to the graphics controller 120 identifying the gate to be displayed on or manipulated via the display device 106 (e.g., by clicking on or in the desired gate when the cursor is positioned there).

After receiving the gate selection signal, the graphics controller 120 may be configured to receive a triggering event from a second input device. The second input device may be implemented as a keyboard 108. The keyboard 108 may control changes in plot visualization by sending a signal identifying a triggering event to the graphics controller 120. For example, activation of a specific key or group of keys on the keyboard 108 may generate a specific triggering event. In response to the triggering event, the graphics controller 120 may be configured to replace the first plot displayed on the display device 106 with a second plot while maintaining and/or manipulating the gate, for example, allowing a user to cycle through various plots of biological event data while maintaining and/or manipulating a gate.

The first and second input devices may be implemented as one or more of the mouse 110, the keyboard 108, or other means for providing an input signal to the graphics controller 120 such as a touchscreen, a stylus, an optical detector, or a voice recognition system. Some input devices may include multiple inputting functions. In such implementations, the inputting functions may each be considered an input device. For example, as shown in FIG. 1, the mouse 110 includes a right mouse button 112 and a left mouse button 113, each of which may generate a triggering event.

The triggering event may cause the graphics controller 120 to alter the manner in which the data is displayed or which portions of the data is actually displayed on the display device 106 or both at the same time.

In some embodiments, the graphics controller 120 may be configured to detect when gate selection is initiated by the mouse 110. The graphics controller 120 may be further configured to automatically modify plot visualization to optimally facilitate the gating process. The modification may be based on the specific distribution of biological event data received by the graphics controller 120.

The graphics controller 120 may be connected to a storage device 104. The storage device 104 may be configured to receive and store biological event data from the graphics controller 120. The storage device 104 may also be configured to receive and store flow cytometric event data from the graphics controller 120. The storage device 104 may be further configured to allow retrieval of biological event data, such as flow cytometric event data, by the graphics controller 120.

A display device 106 may be configured to receive display data from the graphics controller 120. The display data may comprise plots of biological event data and gates outlining sections of the plots. The display device 106 may be further configured to alter the information presented according to input received from the graphics controller 120 in conjunction with input from the particle analyzer 102, the storage device 104, the keyboard 108, and/or the mouse 110.

A common flow sorting technique which may be referred to as "electrostatic cell sorting," utilizes droplet sorting in which a stream or moving fluid column containing linearly segregated particles is broken into drops and the drops containing particles of interest are electrically charged and deflected into a collection tube by passage through an electric field. Current drop sorting systems are capable of forming drops at a rate of 100,000 drops/second in a fluid stream that is passed through a nozzle having a diameter less than 100 micrometers. Droplet sorting typically requires that the drops break off from the stream at a fixed distance from the nozzle tip. The distance is normally on the order of a few millimeters from the nozzle tip and can be stabilized and maintained for an unperturbed fluid stream by oscillating the nozzle tip at a predefined frequency with an amplitude to hold the break-off constant. For example, in some embodiments, adjusting amplitude of a sine wave shaped voltage pulse at a given frequency holds the break-off stable and constant.

Typically, the linearly entrained particles in the stream are characterized as they pass through an observation point situated within a flow cell or cuvette, or just below the nozzle tip. Once a particle is identified as meeting one or more desired criteria, the time at which it will reach the drop break-off point and break from the stream in a drop can be predicted. Ideally, a brief charge is applied to the fluid stream just before the drop containing the selected particle breaks from the stream and then grounded immediately after the drop breaks off. The drop to be sorted maintains an electrical charge as it breaks off from the fluid stream, and all other drops are left uncharged. The charged drop is deflected sideways from the downward trajectory of the other drops by an electrical field and collected in a sample tube. The uncharged drops fall directly into a drain.

Figure 2A:
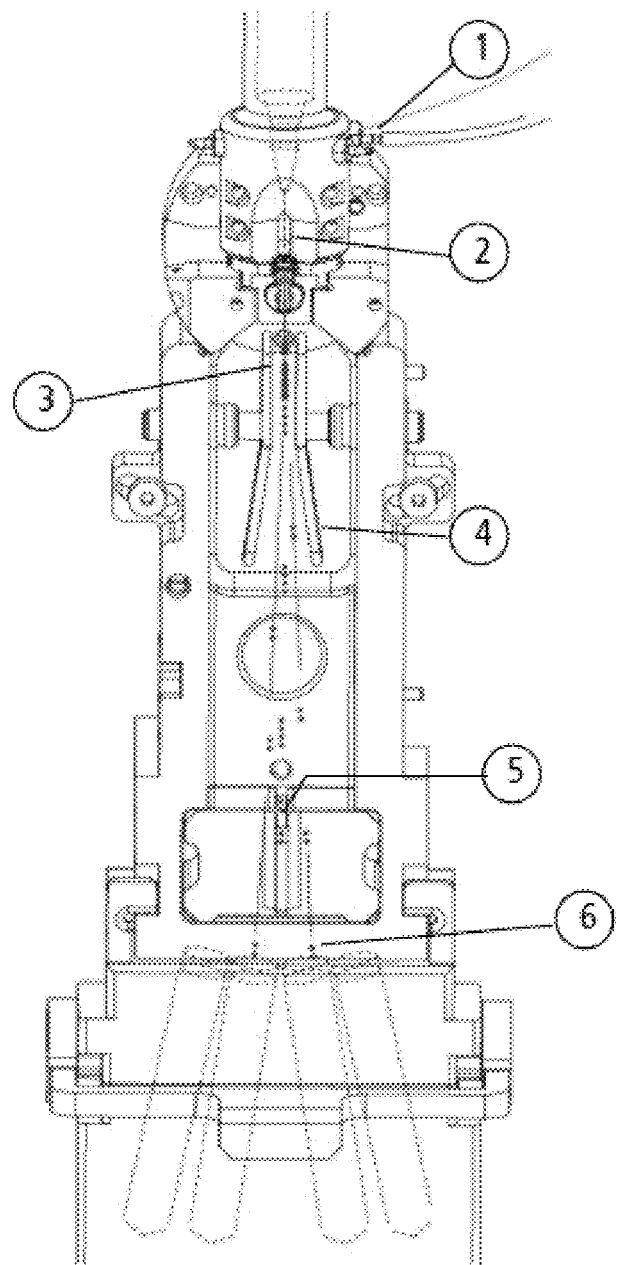
FIG. 2A and FIG. 2B are schematic drawings of particle sorter systems in accordance with one or more embodiments presented herein.

FIG. 2A is a schematic drawing of a particle sorter system, in accordance with one embodiment presented herein. At 1, a charge is applied via a stream-charging wire in a barb. At 2, a sample generates light scatter and a fluorescence signal. The signal is analyzed. At 3, a charged droplet breaks off. At 4, deflection plates attract or repel the charged droplet to guide the droplet toward a destination collection receptacle. At 5, uncharged droplets pass into a waste receptacle. At 6, charged drops containing particles of interest are collected in one or more corresponding collection receptacles. Sorting electronics may be included to initiate collection of measurements, receive fluorescence signals for particles, and determine how to adjust the deflection plates to cause sorting of the particles. Example implementations of the embodiment shown in FIG. 2A include the BD FACSAria™ line of flow cytometers commercially provided by Becton, Dickinson and Company of San Jose, Calif.

Figure 2B:
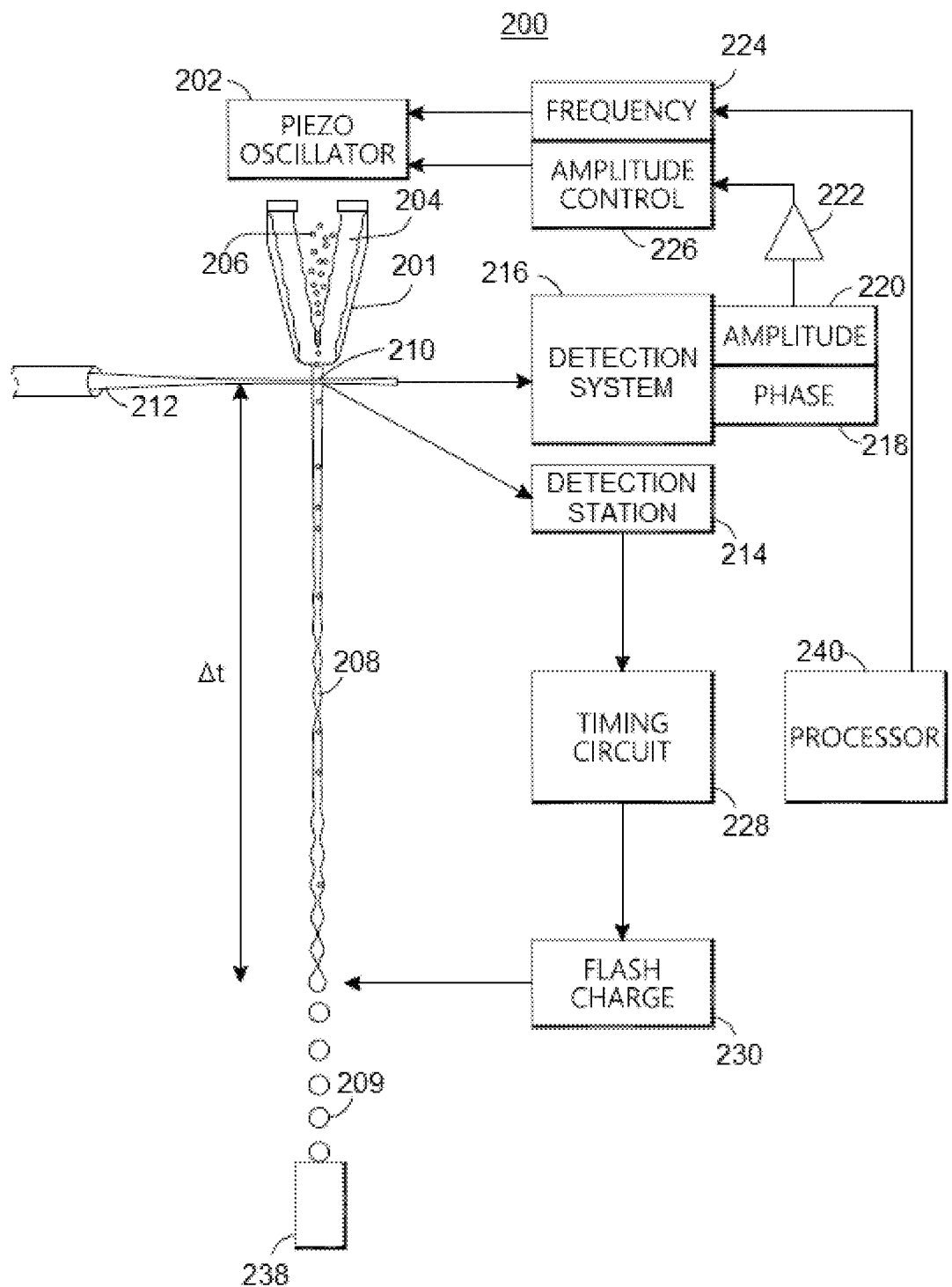

FIG. 2B is a schematic drawing of a particle sorter system 200, in accordance with one embodiment presented herein. In some embodiments, the particle sorter system 200 is a cell sorter system. As shown in FIG. 2B, a drop formation transducer 202 (e.g., piezo-oscillator) is coupled to a fluid conduit 201 such as nozzle. Within fluid conduit 201, sheath fluid 204 hydrodynamically focuses a sample fluid 206 into a moving fluid column 208 (e.g. stream). Within the moving fluid column 208, particles (e.g., cells) are lined up in single file to cross a monitored area 210 (e.g., laser-stream intersect), irradiated by an irradiation source 212 (e.g., laser). Vibration of the drop formation transducer 202 causes moving fluid column 208 to break into a plurality of drops 209.

In operation, a detection station 214 (e.g., event detector) identifies when a particle of interest (or cell of interest) crosses monitored area 210. Detection station 214 feeds into timing circuit 228, which in turn feeds into flash charge circuit 230. At a drop break off point, informed by a timed drop delay (at), a flash charge is applied to the moving fluid column 208 such that a drop of interest carries a charge. The drop of interest may include one or more particles or cells to be sorted. The charged drop can then be sorted by activating deflection plates (not shown) to deflect the drop into a vessel such as a collection tube or a multi-well sample plate where a well may be associated with drops of particular interest. As shown in FIG. 2B, however, the drops are collected in a drain receptacle 238.

A detection system 216 (e.g. drop boundary detector) serves to automatically determine the phase of a drop drive signal when a particle of interest passes the monitored area 210. An exemplary drop boundary detector is described in U.S. Pat. No. 7,679,039, which is incorporated herein by reference in its entirety. Detection system 216 allows the instrument to accurately calculate the place of each detected particle in a drop. Detection system 216 may feed into an amplitude signal 220 and/or phase 218 signal, which in turn feeds (via amplifier 222) into an amplitude control circuit 226 and/or frequency control circuit 224. Amplitude control circuit 226 and/or frequency control circuit 224, in turn, controls the drop formation transducer 202. The amplitude control circuit 226 and/or frequency control circuit 224 may be included in a control system.

In some implementations, sort electronics (e.g., the detection system 216, the detection station 214 and a processor 240) may be coupled with a memory configured to store the detected events and a sort decision based thereon. The sort decision may be included in the event data for a particle. In some implementations, the detection system 216 and the detection station 214 may be implemented as a single detection unit or communicatively coupled such that an event measurement may be collected by one of the detection system 216 or the detection station 214 and provided to the non-collecting element.

In some embodiments, one or more components described for the particle sorter system 200 may be used to analyze and characterize particles, with or without physically sorting the particles into collection vessels. Likewise, one or more components described below for the particle analysis system 300 (FIG. 3) may be used to analyze and characterize particles, with or without physically sorting the particles into collection vessels. For example, particles may be grouped or displayed in a tree that includes at least three groups as described herein, using one or more of the components of the particle sorter system 200 or particle analysis system 300.

Figure 3:
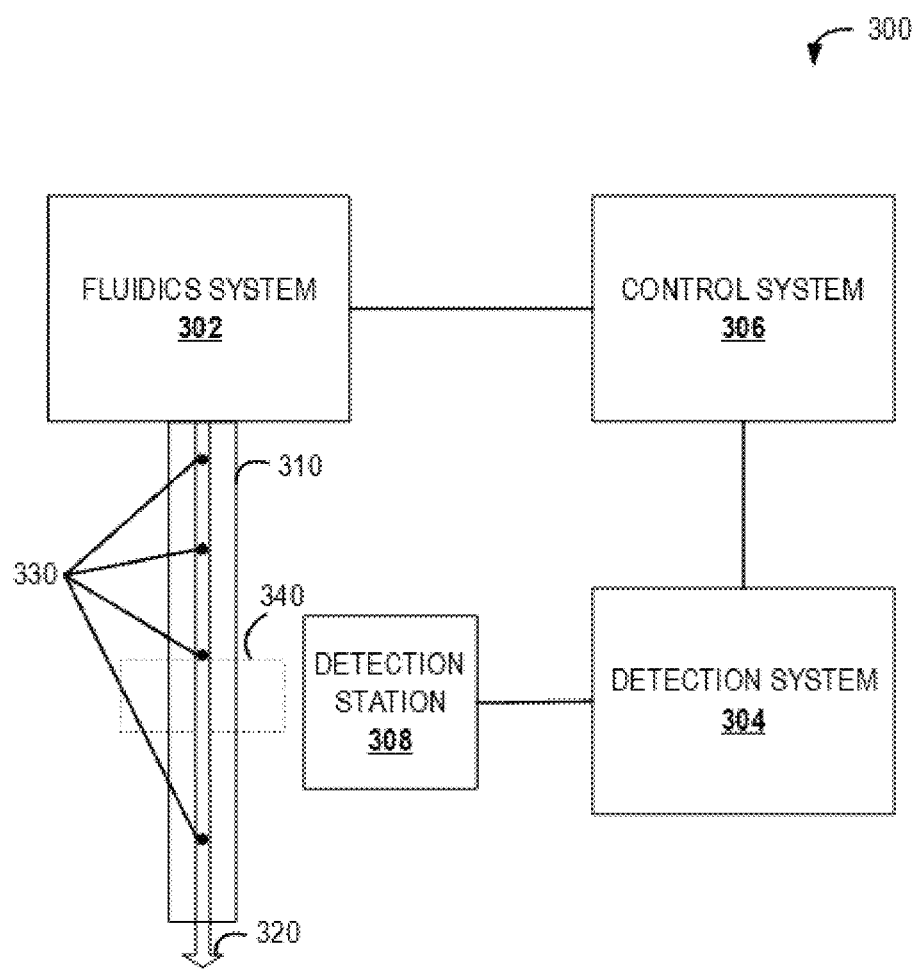
FIG. 3 shows a functional block diagram of a particle analysis system for computational based sample analysis and particle characterization.

FIG. 3 shows a functional block diagram of a particle analysis system for computational based sample analysis and particle characterization. In some embodiments, the particle analysis system 300 is a flow system. The particle analysis system 300 shown in FIG. 3 may be configured to perform, in whole or in part, the methods described herein such as, for example, the method of FIG. 5 or the method of FIG. 8. The particle analysis system 300 includes a fluidics system 302. The fluidics system 302 may include or be coupled with a sample tube 310 and a moving fluid column within the sample tube in which particles 330 (e.g. cells) of a sample move along a common sample path 320.

The particle analysis system 300 includes a detection system 304 configured to collect a signal from each particle as it passes one or more detection stations along the common sample path. A detection station 308 generally refers to a monitored area 340 of the common sample path. Detection may, in some implementations, include detecting light or one or more other properties of the particles 330 as they pass through a monitored area 340. In FIG. 3, one detection station 308 with one monitored area 340 is shown. Some implementations of the particle analysis system 300 may include multiple detection stations. Furthermore, some detection stations may monitor more than one area.

Each signal is assigned a signal value to form a data point for each particle. As described above, this data may be referred to as event data. The data point may be a multidimensional data point including values for respective properties measured for a particle. The detection system 304 is configured to collect a succession of such data points in a first time interval.

The particle analysis system 300 also includes a control system 306. The control system 306 may include one or more processors, an amplitude control circuit 226 and/or a frequency control circuit 224 as shown in FIG. 2B. The control system 306 shown is operationally associated with the fluidics system 302. The control system 306 configured to generate a calculated signal frequency for at least a portion of the first time interval based on a Poisson distribution and the number of data points collected by the detection system 804 during the first time interval. The control system 306 is further configured to generate an experimental signal frequency based on the number of data points in the portion of the first time interval. The control system 306 additionally compares the experimental signal frequency with that of a calculated signal frequency or a predetermined signal frequency.

Figure 4:
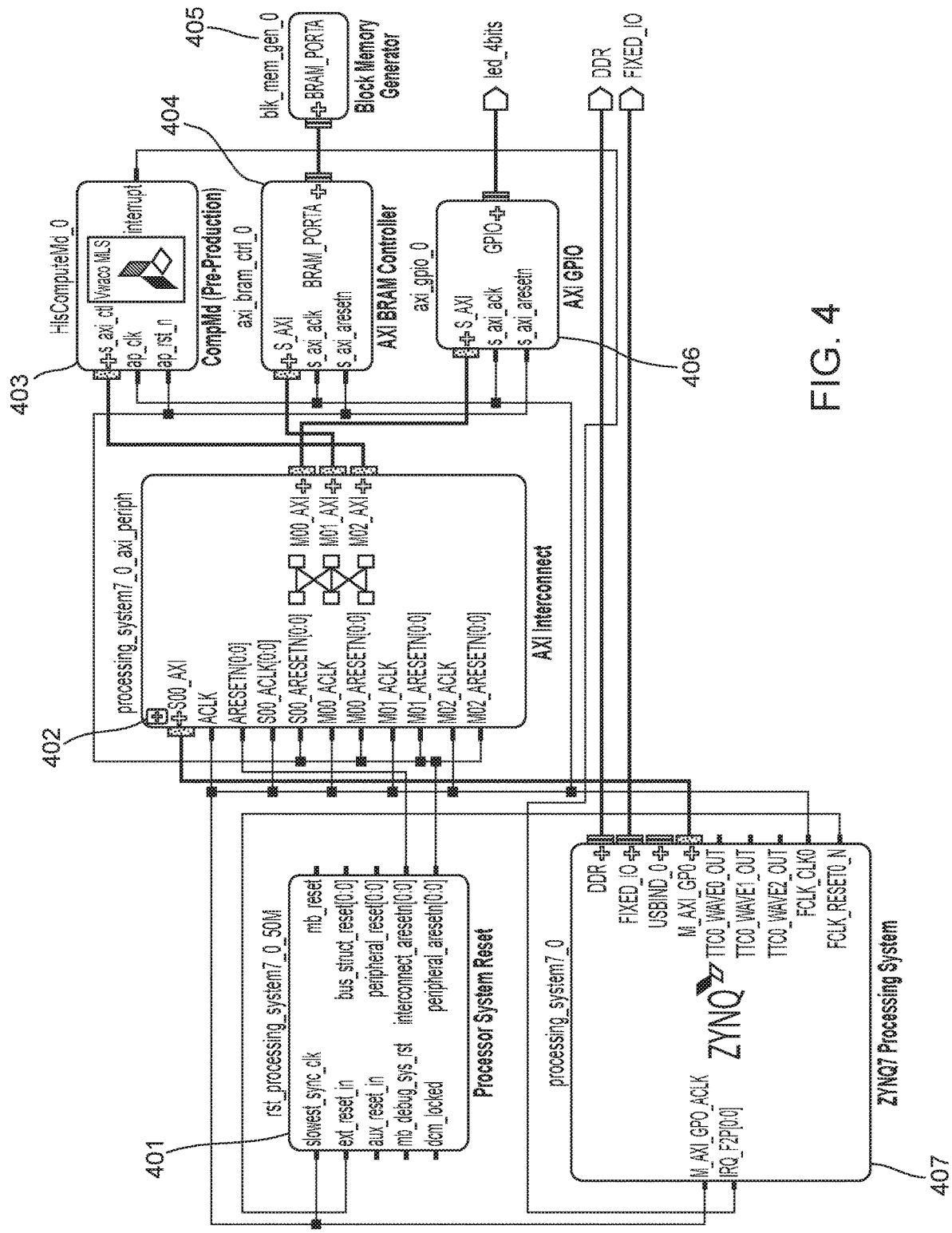
FIG. 4 is a diagram showing an example electronics configuration to implement one or more of the embodiments described.
Figure 5:
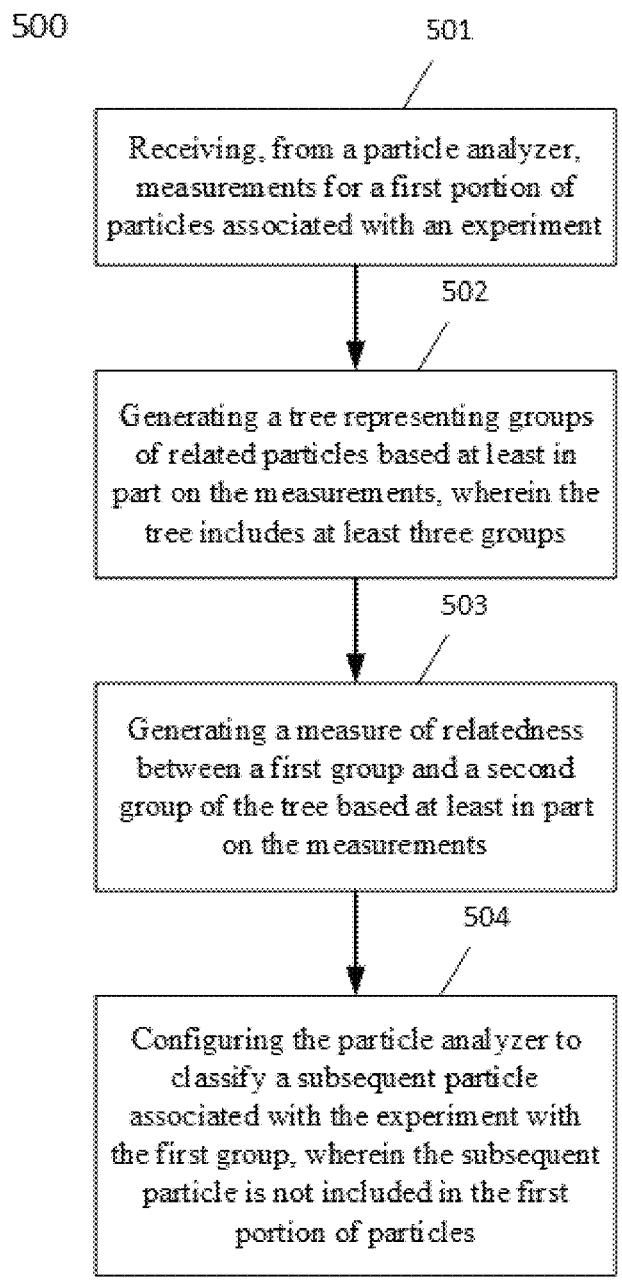
FIG. 5 is a process flow diagram depicting an example of a method of computational based sample analysis and particle characterization.
Figure 6:
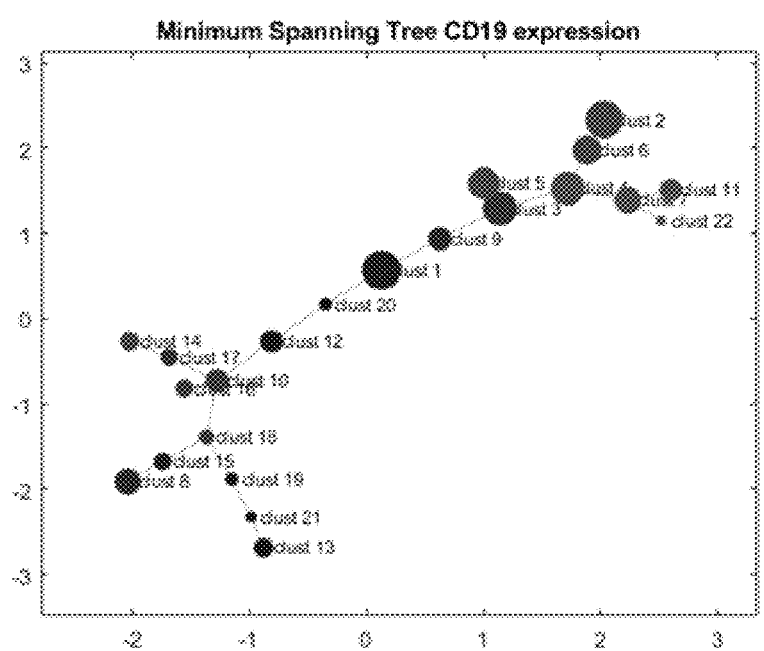
FIG. 6 depicts an example of a minimum spanning tree.
Figure 8:
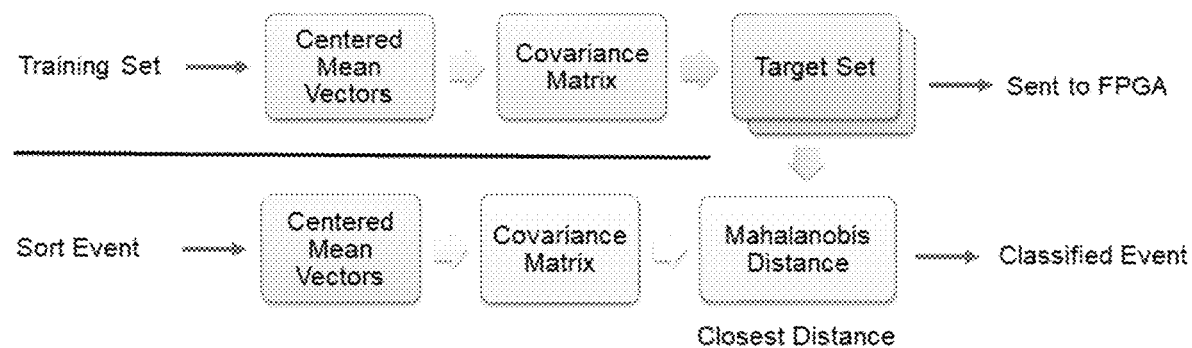
FIG. 8 is a process flow diagram depicting an example method of computational based sample analysis and particle characterization.

FIG. 4 is diagram showing an example electronics configuration to implement one or more embodiments as described herein. For example, the electronics in FIG. 4 may be included in a particle analyzer, such as the particle analyzer 102 shown in FIG. 1. The electronics may implement a method for computational particle analysis and characterization such as depicted in FIG. 5, FIG. 6, or FIG. 8. The electronics in FIG. 4 include a processor system reset 401, an AXI interconnect 402, a block 403 that computes Mahalanobis distances (CompMd) 403, an AxI block random access memory (BRAM) controller 404, a block memory generator 405, an AXI general purpose input/output (GPIO) 406, and a programmable processing system 407 such as a software on a chip, an example of which is the ZYNQ-7000 series commercially available from Xilinx, Inc. of San Jose, Calif. In some embodiments, the CompMd 403 includes a compute engine which can be dynamically programmed to implement sorting logic for a sample being analyzed by the particle analyzer. The compute engine may include a Mahalanobis compute engine. The sorting logic may be defined using the computational analytic features described. In some implementations, the sorting logic may be provided to configure the electronics after collecting and processing measurements for a predetermined number of particles as described. In some implementations, the sorting logic may be updated during an experiment, in response to analysis of measurements of particles from a sample associated with the experiment.

The example shown in FIG. 4, overall, includes a test harness that may be used for development of a Mahalanobis distance computational logic block for implementation on an FPGA. It shows a specific example for a Xilinx Zynq System on Chip (SoC), including an Advanced Extensible Interface (AXI) interconnect for the Processing System (PS) to communicate with the Programmable Logic (PL) where the CompMd performs the distance calculation. The functionality of this configuration includes verification of the CompMd logic block. Once verified, the CompMd block may be imported into a flow cytometer configuration, wired accordingly, where its result is used for making a sort decision. The electronics shown in FIG. 4 may be included in a sorting flow cytometer such as shown in FIG. 2A, 2B, or 3.

In some embodiments, the subject systems are configured to sort components of a sample, such as cells in a biological sample. The term "sorting" is referred to herein in its conventional sense as separating components (e.g., particles such as cells, non-cellular particles including biological macromolecules) of the sample and in some instances delivering the separated components to one or more sample collection containers. For example, the subject systems may be configured for sorting samples having 2 or more components, such as 3 or more components, such as 4 or more components, such as 5 or more components, such as 10 or more components, such as 15 or more components and including soring a sample having 25 or more components.

One or more of the sample components may be separated from the sample and delivered to a sample collection container, such as 2 or more sample components, such as 3 or more sample components, such as 4 or more sample components, such as 5 or more sample components, such as 10 or more sample components and including 15 or more sample components may be separated from the sample and delivered to a sample collection container.

In some embodiments, the subject systems include a particle sorting component for sorting cells of the sample. In certain instances, the particle sorting component is a particle sorting module such as those described in U.S. Patent Publication No. 2017/0299493, filed on Mar. 28, 2017 and U.S. Provisional Patent Application No. 62/752,793 filed on Oct. 30, 2018, the disclosures of which is incorporated herein by reference. In certain embodiments, the particle sorting component include one or more droplet deflectors such as those described in U.S. Patent Publication No. 2018/0095022, filed on Jun. 14, 2017, the disclosure of which is incorporated herein by reference.

In some embodiments, the subject systems are flow cytometric systems for analyzing and sorting particles in a sample (e.g., cells in a biological sample) practicing the methods described herein. Suitable flow cytometry systems may include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49 (pt 1):17-28; Linden, et. al., *Semin Thromb Hemost.* 2004 October; 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ II flow cytometer, BD Accuri™ flow cytometer, BD Biosciences FACSCelesta™ flow cytometer, BD Biosciences FACSLyric™ flow cytometer, BD Biosciences FACSVerse™ flow cytometer, BD Biosciences FACSymphony™ flow cytometer BD Biosciences LSRFortessa™ flow cytometer, BD Biosciences LSRFortess™ X-20 flow cytometer and BD Biosciences FACSCalibur™ cell sorter, a BD Biosciences FACSCount™ cell sorter, BD Biosciences FACSLyric™ cell sorter and BD Biosciences Via™ cell sorter BD Biosciences Influx™ cell sorter, BD Biosciences Jazz™ cell sorter, BD Biosciences Aria™ cell sorters and BD Biosciences FACSMelody™ cell sorter, or the like.

In some embodiments, the subject particle sorting systems are flow cytometric systems, such those described in U.S. Pat. Nos. 10,006,852; 9,952,076; 9,933,341; 9,784,661; 9,726,527; 9,453,789; 9,200,334; 9,097,640; 9,095,494; 9,092,034; 8,975,595; 8,753,573; 8,233,146; 8,140,300; 7,544,326; 7,201,875; 7,129,505; 6,821,740; 6,813,017; 6,809,804; 6,372,506; 5,700,692; 5,643,796; 5,627,040; 5,620,842; 5,602,039; the disclosure of which are herein incorporated by reference in their entirety.

In certain instances, the subject systems are flow cytometry systems configured for imaging particles in a flow stream by fluorescence imaging using radiofrequency tagged emission (FIRE), such as those described in Diebold, et al. *Nature Photonics Vol.* 7(10); 806-810 (2013) as well as described in U.S. Pat. Nos. 9,423,353; 9,784,661 and 10,006,852 and U.S. Patent Publication Nos. 2017/0133857 and 2017/0350803, the disclosures of which are herein incorporated by reference.

Methods for Characterizing Particles of a Sample

As summarized above, aspects of the present disclosure include methods for characterizing particles from a particle analyzer. Methods according to certain embodiments include under control of one or more processing devices, receiving, from a particle analyzer, measurements for a first portion of particles associated with an experiment; generating a tree representing groups of related particles based at least in part on the measurements, wherein the tree includes at least three groups; generating a measure of relatedness between a first group and a second group of the tree based at least in part on the measurements; and configuring the particle analyzer to classify a subsequent particle associated with the experiment with the first group, wherein the subsequent particle is not included in the first portion of particles.

In practicing methods according to certain embodiments, a sample having particles is irradiated with a light source and light from the sample is detected to generate a tree representing groups of related particles based at least in part on the measurements of the detected light. In some instances, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In practicing the subject methods, a sample having particles (e.g., in a flow stream of a flow cytometer) is irradiated with light from a light source. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Where methods include irradiating with a broadband light source, broadband light source protocols of interest may include, but are not limited to, a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, methods includes irradiating with a narrow band light source emitting a particular wavelength or a narrow range of wavelengths, such as for example with a light source which emits light in a narrow range of wavelengths like a range of 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Where methods include irradiating with a narrow band light source, narrow band light source protocols of interest may include, but are not limited to, a narrow wavelength LED, laser diode or a broadband light source coupled to one or more optical bandpass filters, diffraction gratings, monochromators or any combination thereof.

In certain embodiments, methods include irradiating the flow stream with one or more lasers. As discussed above, the type and number of lasers will vary depending on the sample as well as desired light collected and may be a pulsed laser or continuous wave laser. For example, the laser may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof; a dye laser, such as a stilbene, coumarin or rhodamine laser; a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof; a solid-state laser, such as a ruby laser, an Nd:YAG laser, NdCrYAG laser, Er:YAG laser, Nd:YLF laser, Nd:YVO4 laser, $Nd:YCa_4O(BO_3)_3$ laser, Nd:YCOB laser, titanium sapphire laser, thulim YAG laser, ytterbium YAG laser, ytterbium203 laser or cerium doped lasers and combinations thereof; a semiconductor diode laser, optically pumped semiconductor laser (OPSL), or a frequency doubled- or frequency tripled implementation of any of the above mentioned lasers.

The sample may be irradiated with one or more of the above-mentioned light sources, such as 2 or more light sources, such as 3 or more light sources, such as 4 or more light sources, such as 5 or more light sources and including 10 or more light sources. The light source may include any combination of types of light sources. For example, in some embodiments, the methods include irradiating the sample in the flow stream with an array of lasers, such as an array having one or more gas lasers, one or more dye lasers and one or more solid-state lasers.

The sample may be irradiated with wavelengths ranging from 200 nm to 1500 nm, such as from 250 nm to 1250 nm, such as from 300 nm to 1000 nm, such as from 350 nm to 900 nm and including from 400 nm to 800 nm. For example, where the light source is a broadband light source, the sample may be irradiated with wavelengths from 200 nm to 900 nm. In other instances, where the light source includes a plurality of narrow band light sources, the sample may be irradiated with specific wavelengths in the range from 200 nm to 900 nm. For example, the light source may be plurality of narrow band LEDs (1 nm-25 nm) each independently emitting light having a range of wavelengths between 200 nm to 900 nm. In other embodiments, the narrow band light source includes one or more lasers (such as a laser array) and the sample is irradiated with specific wavelengths ranging from 200 nm to 700 nm, such as with a laser array having gas lasers, excimer lasers, dye lasers, metal vapor lasers and solid-state laser as described above.

Where more than one light source is employed, the sample may be irradiated with the light sources simultaneously or sequentially, or a combination thereof. For example, the sample may be simultaneously irradiated with each of the light sources. In other embodiments, the flow stream is sequentially irradiated with each of the light sources. Where more than one light source is employed to irradiate the sample sequentially, the time each light source irradiates the sample may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the sample with the light source (e.g. laser) for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where sample is sequentially irradiated with two or more light sources, the duration sample is irradiated by each light source may be the same or different.

The time period between irradiation by each light source may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each light source is 10 microseconds. In embodiments where sample is sequentially irradiated by more than two (i.e., 3 or more) light sources, the delay between irradiation by each light source may be the same or different.

The sample may be irradiated continuously or in discrete intervals. In some instances, methods include irradiating the sample in the sample with the light source continuously. In other instances, the sample in is irradiated with the light source in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the light source, the sample may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

In practicing the subject methods, light from the irradiated sample is measured, such as by collecting light from the sample over a range of wavelengths (e.g., 200 nm-1000 nm). In embodiments, methods may include one or more of measuring light absorption by the sample (e.g., brightfield light data), measuring light scatter (e.g., forward or side scatter light data) and measuring light emission by the sample (e.g., fluorescence light data).

Light from the sample may be measured at one or more wavelengths of, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the collected light at 400 or more different wavelengths. Light may be collected over one or more of the wavelength ranges of 200 nm-1200 nm. In some instances, methods include measuring the light from the sample over a range of wavelengths, such as from 200 nm to 1200 nm, such as from 300 nm to 1100 nm, such as from 400 nm to 1000 nm, such as from 500 nm to 900 nm and including from 600 nm to 800 nm. In other instances, methods include measuring collected light at one or more specific wavelengths. For example, the collected light may be measured at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, methods including measuring wavelengths of light which correspond to the fluorescence peak wavelength of certain fluorophores.

The collected light may be measured continuously or in discrete intervals. In some instances, methods include taking measurements of the light continuously. In other instances, the light is measured in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Measurements of the collected light may be taken one or more times during the subject methods, such as 2 or more times, such as 3 or more times, such as 5 or more times and including 10 or more times. In certain embodiments, light from the sample is measured 2 or more times, with the data in certain instances being averaged.

In some embodiments, methods include further adjusting the light from the sample before detecting the light. For example, the light from the sample source may be passed through one or more lenses, mirrors, pinholes, slits, gratings, light refractors, and any combination thereof. In some instances, the collected light is passed through one or more focusing lenses, such as to reduce the profile of the light. In other instances, the emitted light from the sample is passed through one or more collimators to reduce light beam divergence.

In certain embodiments, methods include irradiating the sample with two or more beams of frequency shifted light. As described above, a light beam generator component may be employed having a laser and an acousto-optic device for frequency shifting the laser light. In these embodiments, methods include irradiating the acousto-optic device with the laser. Depending on the desired wavelengths of light produced in the output laser beam (e.g., for use in irradiating a sample in a flow stream), the laser may have a specific wavelength that varies from 200 nm to 1500 nm, such as from 250 nm to 1250 nm, such as from 300 nm to 1000 nm, such as from 350 nm to 900 nm and including from 400 nm to 800 nm. The acousto-optic device may be irradiated with one or more lasers, such as 2 or more lasers, such as 3 or more lasers, such as 4 or more lasers, such as 5 or more lasers and including 10 or more lasers. The lasers may include any combination of types of lasers. For example, in some embodiments, the methods include irradiating the acousto-optic device with an array of lasers, such as an array having one or more gas lasers, one or more dye lasers and one or more solid-state lasers.

Where more than one laser is employed, the acousto-optic device may be irradiated with the lasers simultaneously or sequentially, or a combination thereof. For example, the acousto-optic device may be simultaneously irradiated with each of the lasers. In other embodiments, the acousto-optic device is sequentially irradiated with each of the lasers. Where more than one laser is employed to irradiate the acousto-optic device sequentially, the time each laser irradiates the acousto-optic device may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the acousto-optic device with the laser for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where the acousto-optic device is sequentially irradiated with two or more lasers, the duration the acousto-optic device is irradiated by each laser may be the same or different.

The time period between irradiation by each laser may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each laser is 10 microseconds. In embodiments where the acousto-optic device is sequentially irradiated by more than two (i.e., 3 or more) lasers, the delay between irradiation by each laser may be the same or different.

The acousto-optic device may be irradiated continuously or in discrete intervals. In some instances, methods include irradiating the acousto-optic device with the laser continuously. In other instances, the acousto-optic device is irradiated with the laser in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the laser, the acousto-optic device may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

In embodiments, methods include applying radiofrequency drive signals to the acousto-optic device to generate angularly deflected laser beams. Two or more radiofrequency drive signals may be applied to the acousto-optic device to generate an output laser beam with the desired number of angularly deflected laser beams, such as 3 or more radiofrequency drive signals, such as 4 or more radiofrequency drive signals, such as 5 or more radiofrequency drive signals, such as 6 or more radiofrequency drive signals, such as 7 or more radiofrequency drive signals, such as 8 or more radiofrequency drive signals, such as 9 or more radiofrequency drive signals, such as 10 or more radiofrequency drive signals, such as 15 or more radiofrequency drive signals, such as 25 or more radiofrequency drive signals, such as 50 or more radiofrequency drive signals and including 100 or more radiofrequency drive signals.

The angularly deflected laser beams produced by the radiofrequency drive signals each have an intensity based on the amplitude of the applied radiofrequency drive signal. In some embodiments, methods include applying radiofrequency drive signals having amplitudes sufficient to produce angularly deflected laser beams with a desired intensity. In some instances, each applied radiofrequency drive signal independently has an amplitude from about 0.001 V to about 500 V, such as from about 0.005 V to about 400 V, such as from about 0.01 V to about 300 V, such as from about 0.05 V to about 200 V, such as from about 0.1 V to about 100 V, such as from about 0.5 V to about 75 V, such as from about 1 V to 50 V, such as from about 2 V to 40 V, such as from 3 V to about 30 V and including from about 5 V to about 25 V. Each applied radiofrequency drive signal has, in some embodiments, a frequency of from about 0.001 MHz to about 500 MHz, such as from about 0.005 MHz to about 400 MHz, such as from about 0.01 MHz to about 300 MHz, such as from about 0.05 MHz to about 200 MHz, such as from about 0.1 MHz to about 100 MHz, such as from about 0.5 MHz to about 90 MHz, such as from about 1 MHz to about 75 MHz, such as from about 2 MHz to about 70 MHz, such as from about 3 MHz to about 65 MHz, such as from about 4 MHz to about 60 MHz and including from about 5 MHz to about 50 MHz.

In these embodiments, the angularly deflected laser beams in the output laser beam are spatially separated. Depending on the applied radiofrequency drive signals and desired irradiation profile of the output laser beam, the angularly deflected laser beams may be separated by 0.001 μm or more, such as by 0.005 μm or more, such as by 0.01 μm or more, such as by 0.05 μm or more, such as by 0.1 μm or more, such as by 0.5 μm or more, such as by 1 μm or more, such as by 5 μm or more, such as by 10 μm or more, such as by 100 μm or more, such as by 500 μm or more, such as by 1000 μm or more and including by 5000 μm or more. In some embodiments, the angularly deflected laser beams overlap, such as with an adjacent angularly deflected laser beam along a horizontal axis of the output laser beam. The overlap between adjacent angularly deflected laser beams (such as overlap of beam spots) may be an overlap of 0.001

μm or more, such as an overlap of 0.005 μm or more, such as an overlap of 0.01 μm or more, such as an overlap of 0.05 μm or more, such as an overlap of 0.1 μm or more, such as an overlap of 0.5 μm or more, such as an overlap of 1 μm or more, such as an overlap of 5 μm or more, such as an overlap of 10 μm or more and including an overlap of 100 μm or more.

In certain instances, the flow stream is irradiated with a plurality of beams of frequency-shifted light and a cell in the flow stream is imaged by fluorescence imaging using radiofrequency tagged emission (FIRE) to generate a frequency-encoded image, such as those described in Diebold, et al. *Nature Photonics* Vol. 7(10); 806-810 (2013) as well as described in U.S. Pat. Nos. 9,423,353; 9,784,661 and 10,006,852 and U.S. Patent Publication Nos. 2017/0133857 and 2017/0350803, the disclosures of which are herein incorporated by reference.

In embodiments, methods include generating a tree representing groups of related particles based at least in part on the measurements of the detected light. The tree representing groups of related particles may be generated from detected light absorption, detected light scatter, detected light emission or any combination thereof. In some instances, the measurements of detected light is from light absorption by the sample, such as from a brightfield light detector. In other instances, the measurements of detected light is light scatter from the sample, such as from a side scatter detector, a forward scatter detector or a combination of a side scatter detector and forward scatter detector. In yet other instances, the measurements of detected light is emitted light from the sample, such as light from fluorophores added to the sample. In still other instances, the measurements of detected light is a combination of detected light absorption, detected light scatter and detected light emission.

Some embodiments of the method further include receiving gate information identifying a range of measurements for classifying the subsequent particle, wherein the first group is defined by the gate information.

Some embodiments of the method include unsupervised learning, wherein the first group is defined by the gate information. In some embodiments, the method includes receiving gate information identifying a range of measurements for classifying the subsequent particle, wherein the first group is defined by the gate information; determining that a difference between a result of the unsupervised learning, and the gate information, corresponds to a threshold; and causing display of an alert identifying the difference.

In some embodiments, the method includes generating the measure of relatedness between the first group and the second group based at least in part on a probability density function to characterize event distances between events included in the first group and the second group. In some embodiments, the probability density function includes a Euclidean distance function. In some embodiments, the probability density function comprises a Mahalanobis distance function. Some embodiments of the method include receiving an inclusion threshold for the first group, wherein the inclusion threshold identifies a first range of measurements for including an unclassified particle in the first group relative to the first group; and receiving an exclusion threshold for the first group, wherein the exclusion threshold identifies a second range of measurements for excluding the unclassified particle from the first group relative to the second group; wherein the subsequent particle is classified with the first group based at least in part on the inclusion threshold and the exclusion threshold.

Some embodiments of the method include generating a covariance matrix based at least in part on a likelihood of an association between the subsequent particle and each of the first group and the second group; wherein configuring the particle analyzer includes adjusting a sorting circuit included in the particle analyzer based at least in part on the covariance matrix. In some embodiments, the sorting circuit is a field programmable gate array.

In some embodiments, the measurements received from the particle analyzer include measurements of light emitted fluorescently by the first portion of particles. In some embodiments, the light emitted fluorescently by the first portion of particles includes light emitted fluorescently by antibodies bound to the first portion of particles.

In some embodiments, generating the measure of relatedness is performed only for the first and second groups of the tree. Some embodiments include directing the subsequent particle to a collection vessel.

FIG. 5 is a process flow diagram depicting an example of a method. The method 500 allows computational based sample analysis and particle characterization. In some embodiments, the method 500 is computer-implemented. In some embodiments, the method 500 is under control of one or more processing devices. The method 500 may be implemented in whole or in part using a controlling device which may be implemented using one or more of the devices shown, such as those shown in FIGS. 1-4.

At block 501, a controlling device may receive, from a particle analyzer, measurements for a first portion of particles associated with an experiment. The measurements may include one or more of light, sound, or image measurements. In some embodiments, the light includes light that is scattered or fluoresced by one or more particles. For example, the light may include side scattered or forward scattered laser light. In some embodiments, the measurements received from the particle analyzer include measurements of light emitted fluorescently by the first portion of particles. In some embodiments, the measurements relate to the size or complexity of one or more particles.

The first portion of particles may be identified based on a threshold measurement count. For example, the first portion of particles may correspond to the first 50,000 measurements collected for a sample. In some embodiments, the particles include one or more cells. In some embodiments, the cells include viable cells. The cells may be eukaryotic, prokaryotic, or archaic cells. In some embodiments, the cells include mammalian cells. In some embodiments, the cells include human cells. In some embodiments, the cells include hematopoietic cells. In some embodiments, the cells include B cells or immune cells. In some embodiments, one or more of the cells displays a marker that may be recognized by an antibody or other receptor. In some embodiments, the cells are stained by a fluorescently-labeled antibody that recognizes a marker one or more of the cells. In some embodiments, the measurements relate to the amount of light fluorescence emitted by the stained cells.

Some embodiments include receiving gate information identifying a range of measurements for classifying the subsequent particle, wherein the first group is defined by the gate information. In some embodiments, the gate information is defined at least in part by a user selection such as a polygon drawn on a graphical user interface. In some embodiments, the gate information is defined by unsupervised learning. For example, the method 500 may include unsupervised learning to define the gate information. Some embodiments include unsupervised learning, where the first group is defined by the gate information. Some embodiments include receiving gate information identifying a range of measurements for classifying the subsequent particle, where the first group is defined by the gate information, determining that a difference between a result of the unsupervised learning, and the gate information, corresponds to a threshold, and causing display of an alert identifying the difference.

In some embodiments, the first portion of particles includes a training set of particles. For example, the training set may be used to generate gates or other information for use in classifying or sorting one or more subsequent particles. In some embodiments, the first portion of particles includes thousands, tens of thousands, hundreds of thousands, or millions of particles. In some embodiments, thousands, tens of thousands (for example, 50,000), hundreds of thousands, or millions of subsequent particles are classified. Each of these particles may also be sorted based on its classification.

At block 502, the controlling device may identify groups of related particles based at least in part on the measurements. Identifying the related particles may include generating a tree representing groups of related particles based at least in part on the measurements, wherein the tree includes at least three groups. Some embodiments include generating a tree representing groups of particles and their relationship to each other based at least in part on the measurements, wherein the tree includes at least three groups. The groups may also be referred to as "nodes" or "clusters." In some embodiments, the tree includes more than three groups, for example, 4, 9, 10, 11, 22, 23, 24, 25, 26, 27, 28, 29, 30, or more groups. The description may refer to a tree as the structure for representing the relationships between groups of particles, but alternative or additional structures may be used to represent the relationships such as vectors, hierarchies, referential sets, or the like.

In some embodiments, generating the tree may include one or more of the following: defining populations by manual gating, clustering, or a combination of selected supervised and unsupervised methods; sampling population events within gates and or derived clusters to create covariance (CoV) matrices; using matrix function distance metrics to assess similarity to generate a symmetric adjacency matrix of node similarity distances (for example, Mahalanobis distances from each set to every other set); creating a weighted undirected graph of the population nodes where the node similarity distances become the edge weights; and generating a force directed minimum spanning tree of the nodes in the weighted undirected graph such that the minimum spanning tree represents the subset of the edges of the connected node vertices in the undirected graph that represent the sum of edge weights that is as small as possible. In some embodiments, the force directed minimum spanning tree represents a data driven characterization of the particles included an experiment. The characterization may summarize, based on an initial portion of the particles, the groups of particles expected to be present within a specific sample.

The node similarity distances may indicate a measure of relatedness such as, for example, Mahalanobis distances or Euclidian distances. In some embodiments, the tree is graphically displayed. In some embodiments, the node similarity distances are dynamically represented graphically by the line color, length, or thickness on the display. For example, a line between two closely-related nodes may be one color such as green, and/or may be shorter (for example, about five to ten pixels long) or thicker (for example, three or four pixels wide) than a line between less-related nodes which may be, for example red, fifteen to twenty pixels long and/or one or two pixels wide. In some embodiments, the number of events per node is represented graphically by the size of the node, or by the coloring or shade of the node. In some embodiments, a measurement of a particular (such as, for example, the amount of side scatter light emitted by a fluorescently-labeled particle at a particular wavelength) is represented graphically by the coloring or shade of the node, or by the size of the node.

At block 503, the controlling device may generate a measure of relatedness between a first group and a second group of the tree based at least in part on the measurements. Some embodiments include using a probability density function based on event distances for events in a first group and a second group to generate the measure of relatedness between the first group and the second group. The measure of relatedness may include, for example, Mahalanobis distances or Euclidian distances.

Generating a measure of relatedness between groups may include defining a range of parameters or gates that define each group within measurements of separate parameters such as separate fluorescence indicators for each particle. For example, an experiment may include particles labeled by several fluorophores or fluorescently labeled antibodies, and groups of particles may be defined by thresholds or gates corresponding to one or more fluorescent measurements. In the example, a first group may be defined by a certain range of light scattering for a first fluorophore, and a second group may be defined by a certain range of light scattering for a second fluorophore. If the first and second fluorophores are represented on an x and y axis, respectively, then the gates might appear as boxes around each group of particles, if the information was to be graphically displayed. In such a case, the measure of relatedness may be based upon the distance from the center of the gated box around the first group to the center of the gated box around the second group.

In some embodiments, the tree and/or measures of relatedness between nodes are confirmed or modified by the user in a user-directed confirmation or modification step. For example, an alert may be displayed for the user to confirm whether the nodes of the tree, or any gates generated of used to create the tree, are correct. The alert may be generated after the controlling device generates the degree of relatedness. The confirmation may include clicking a button or making a selection on a user display. Additionally, the user may modify the nodes of the tree or gates used to generate the tree. In some embodiments, an analysis is performed on a training set of particles or cells, and an alert or graphic display notifies the user of the results. The alert may include a visual display, a sound, or a vibration. The graphic display may include a traditional dot plot showing individual or representative events, or a graphic display of the tree. In some embodiments, after the user-directed confirmation or modification step, the tree or any gates used to generate the tree may be modified based on the user's input, and a new tree may be generated. The process may be repeated multiple times. After the user confirms that the tree is correct or sufficient for the user's needs, the tree may then be used to classify additional particles.

In some embodiments, generating the measure of relatedness is performed only for the first and second groups of the tree. For example, in some embodiments, generating the measure of relatedness between the first group and a second group of the tree includes not generating a measure of relatedness between the first group and the third group or between the second group and the third group; or includes a step of excluding the third group from the measure of relatedness. In some embodiments, the tree includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more groups or nodes.

In some embodiments, the method 500 includes generating a measure of relatedness between all or just a portion of the groups or nodes. For example, one or more groups may be excluded when the controlling device generates a measure of relatedness between groups. In some embodiments, when the tree includes several nodes, it may be computationally inefficient and slow down computational processing to compare real-time event (or subsequent particle) data to node distance metrics for all of the nodes. Thus, having a minimum spanning tree (MST) may help identify which nodes are very similar to assure that event distances are calculated between the real-time event (or subsequent particle) and relevant nodes, and to exclude nodes that are so intrinsically different that the chances of an event belonging to the excluded node being classified as a target population or a likely "contaminate" is remote. Thus, in some embodiments, not all node distances are calculated between a real-time event or a subsequent particle, and every node on the MST; instead, only node distances that matter are computed, thus saving computational time and power.

At block 504, the controlling device may configure the particle analyzer to classify a subsequent particle associated with the experiment with the first group, wherein the subsequent particle is not included in the first portion of particles. Classifying a subsequent particle may include using a probability density function approach based on event distances to target populations in n-dimensional space. Examples of probability density functions include Euclidian distances (which assume a linear relationships between groups), Mahalanobis distances (which do not assume a linear relationship), or using one or more training sets (from gates or clusters) to compute desired sort targets.

An example expression of a Euclidian distance is shown in Equation (1).

$$d(p, q) = \sqrt{\begin{array}{l}(p_1 - q_1)^2 + (p_2 - q_2)^2 + \ldots + \\ (p_i - q_i)^2 + \ldots + (p_n - q_n)^2\end{array}}. \quad \text{Equation (1)}$$

where d is distance between points p and q; and
n is the number of dimensions in the data set.

An example expression of a Mahalanobis distance is shown in Equation (2).

$$D_m^2(x) = (x-\mu)^T S^{-1}(x-\mu) \quad \text{Equation (2)}$$

where S is the covariance matrix of a target distribution;
x represents a first vector of event observations having a distribution; and
μ represents a second vector of target set observations having a distribution.

An example of the use of a training set includes generating mean vectors, generating a covariance matrix of the training set, and then using the training set covariance matrix to generate a target set. The use of a training set may include (1) generating a matrix of centered values from a training set where the mean of each column is subtracted from each row element in the column; (2) generating a square covariance matrix of the centered value matrix normalized by n−1, where n is the number of events in the training set; (3) for each event, generating a square covariance matrix of its values centered against the training set column means where n is 1 in the covariance matrix operation; and/or (4) calculating the Mahalanobis distance for each event to the training (e.g., target) set by using the transposed mean differences of the event centered means to the training set centered means $(x-\mu)^T$ times the inverted covariance of the training set S-1 times the matrix of mean differences (x−μ) (In some embodiments, this is the squared Mahalanobis distance $D^2$ for each event to the training (e.g., target) set). In some embodiments, the $D^2$ distances follow a chi-square distribution with the number of dimensions (columns) as the degree of freedom, which may allow for a critical chi-square value to be used to determine the probability that an event belongs to the target set by using the inverted chi-square distribution for probability p and degrees of freedom equal to the number of dimensions (columns) in the data.

Some embodiments include receiving an inclusion threshold for the first group, wherein the inclusion threshold identifies a first range of measurements for including an unclassified particle in the first group relative to the first group; and receiving an exclusion threshold for the first group, wherein the exclusion threshold identifies a second range of measurements for excluding the unclassified particle from the first group relative to the second group; wherein the subsequent particle is classified with the first group or not based on the inclusion threshold and the exclusion threshold. Some embodiments include generating a covariance matrix based at least in part on the likelihood of association between the subsequent particle and each of the first group and the second group; wherein configuring the particle analyzer includes adjusting a sorting circuit included in the particle analyzer based at least in part on the covariance matrix.

An example of a graphically displayed minimum spanning tree is shown in FIG. 6. In the example depicted in FIG. 6, the node size is proportional to the number of events in each node, and shade of each node represents the expression of CD19 (a genetic molecular marker) as indicated by a fluorescent marker and measured as scattered laser light at a particular wavelength. In FIG. 6, nodes 8 and 15 are neighboring B cell populations with similar characteristics. Node 22 is an invariant natural killer T (iNKT) cell population that was identified by the methods described herein, and node 7 is its neighbor closest.

Figure 7:
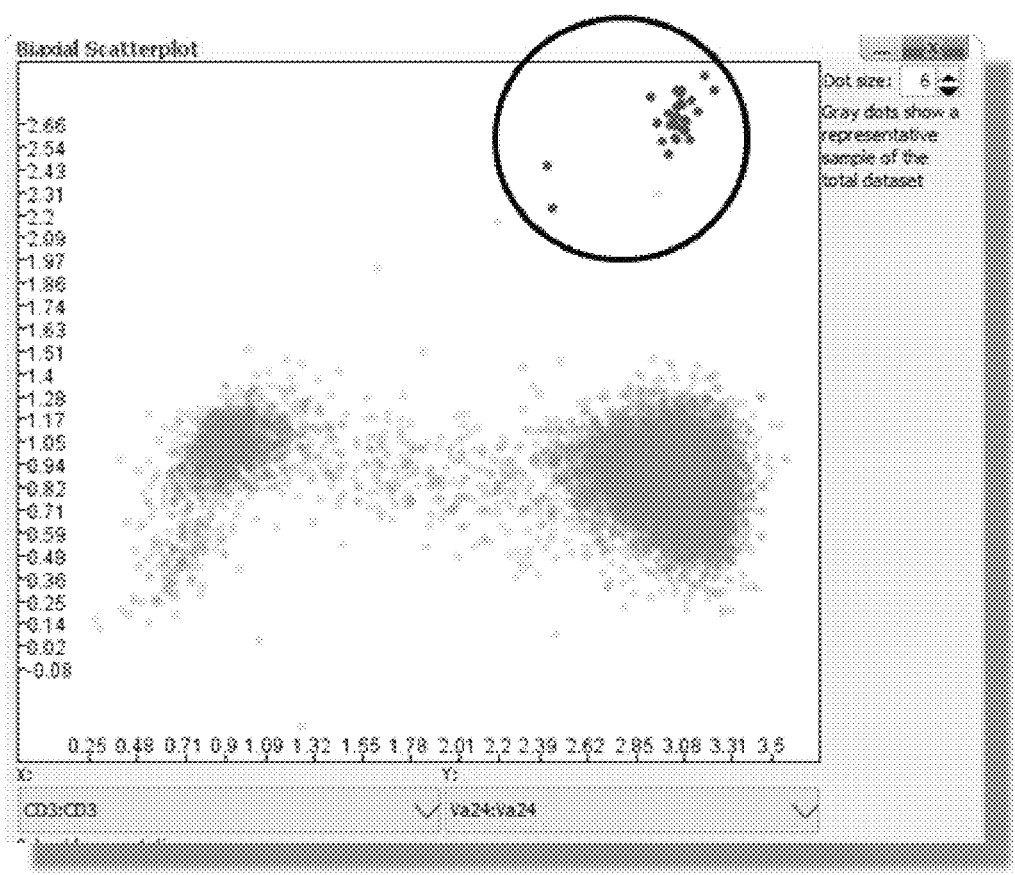
FIG. 7 depicts an example of a biaxial scatterplot showing fluorescence measurements for B cells.

In some embodiments, the data driven scaffold map enables a user to detect cell populations that the user would otherwise disregard. For example, the events circled in FIG. 7 represent a population of iNKT cells that a user might have otherwise disregarded when using standard gating methods. However, the same population of iNKT cells circled in FIG. 7, which might have been disregarded by ordinary methods, was identified by generating a data driven scaffold map as described herein, and is represented in FIG. 6 as node 22. For the examples in FIG. 6 and FIG. 7, the raw data were compensated, transformed (Logicle or Biexponential transformation) and clustered using X-Shift (knn clustering using the Vortex application available from Github, Nikolay Samusik—G Nolab Lab Stanford). The iNKT cells are population cluster 22 in FIG. 6. In FIG. 7, the events in cluster 22 are circled in the scatterplot. Cluster 22 may then be used as the training set.

FIG. 8 is a process flow diagram depicting an example method of computational based sample analysis and particle characterization. The method 500 depicted in FIG. 5 is similar to the method shown in FIG. 8. In some embodiments, the method 500 is computer-implemented. In some embodiments, the method 500 is under control of one or more processing devices. The method 500 may be implemented in whole or in part using a controlling device which may be implemented using one or more of the devices shown, such as those shown in FIGS. 1-4.

The method 800 includes receiving information or measurements for a training set of particles, generating centered mean vectors for the information or measurements in the training set, generating a covariance matrix based on the centered mean vectors, and using the covariance matrix to generate a target set of information. The target set may be generated by its means and covariance, and used in a Mahalanobis distance metric for each new event. The vector of training set means and the covariance matrix (containing the probability distribution of the training set) may be provided to a field programmable gate array (FPGA) included in a particle analyzer. In some cases, the target set may be provided to the FPGA. FIG. 4 includes an example FPGA which may receive and use the target set information. In some embodiments, the CompMd receives target set information and computes Mahalanobis distances. In some embodiments, information relating to a subsequent particle is received and used to generate centered mean vectors, a covariance matrix is generated including information relating to the subsequent particle, Mahalanobis distances are calculated between the subsequent particle and two or more nodes, and the subsequent particle is classified into a group represented by a node with the shortest Mahalanobis distance to the information relating to the subsequent particle.

For example, information relating to the subsequent particle may be measured by the particle analyzer. As the subsequent particle moves down a moving fluid column or stream (as depicted in 208 of FIG. 2B, for example), an FPGA (or other processor) performs matrix and vector math at an ultra-fast rate which allows the subsequent particle to be classified real-time while still in the stream, and then sorted. In some embodiments, the ultra-fast rate of the matrix and vector math is enabled by comparing the Mahalanobis distances (or other relatedness measure) between measurements for the subsequent particle and nodes close to where the subsequent particle is predicted to be, and omitting other nodes calculations. For example, a user may indicate which two nodes the subsequent particle is likely to be near or similar to, and then the FPGA processes and compares the matrix and vector math those two nodes only in comparison to the subsequent particle, and omits other nodes. In some embodiments, a real-time classification and sorting of the subsequent particle is enabled in part by FPGA technology. In some embodiments, classifying subsequent particles in the absence of real-time sorting is sped up by omitting other nodes (or in other words, when a subsequent particle is being classified without being physically sorted). For example, in some embodiments, a measure of relatedness between the first group and a third group of the tree is not generated.

Some embodiments include sorting the subsequent particle into a vessel or collection vessel. Examples of a vessels or collection vessels include tubes, wells, and other containers. In some embodiments, the vessel comprises glass or plastic. In some embodiments, the collection vessel comprises water, a buffered solution or a culture medium. In some embodiments, the vessel includes particles of the first group that are physically separated from particles of a second group. For example, the particles of the second group may be collected in a separate collection vessel from the first group, or may be collected in a drain receptacle or discarded. In some embodiments, the subsequent particle is physically sorted through deflection. For example, the particle may be included in a drop of fluid that is charged and deflected electrostatically by the system in shown in FIG. 2B. In some embodiments, 1, 2, 3, 4, 5, 6, 7, 8, 9, 10, or more collection vessels are included. Several or numerous collection vessels may be included, to any one of which a subsequent particle may be sorted. For example, a subsequent particle or particles may be physically sorted into any one well of a 96-well plate or 365-well plate.

In some embodiments, the methods described herein allow a user to identify more cells within a population than would otherwise have been identified by standard gating techniques, and with more accuracy. For example, by using a covariance matrix with a Mahalanobis distance threshold set at the 95th percentile, 965 cells out of 100,000 raw events were classified as Regulatory T Cells (Tregs; $CD4^+$, $CD25^+$, $CD127^-$), where only 818 Tregs were identified by manual gating. When the Mahalanobis distance threshold was set at the 96th percentile instead of the 95th percentile 1300 Tregs were identified. In the example, X-Shift knn clustering was used, 16 clusters were defined, and an index of five factors (CD4, CD25, CD127, SSC, and FSC) was used.

Figure 9:
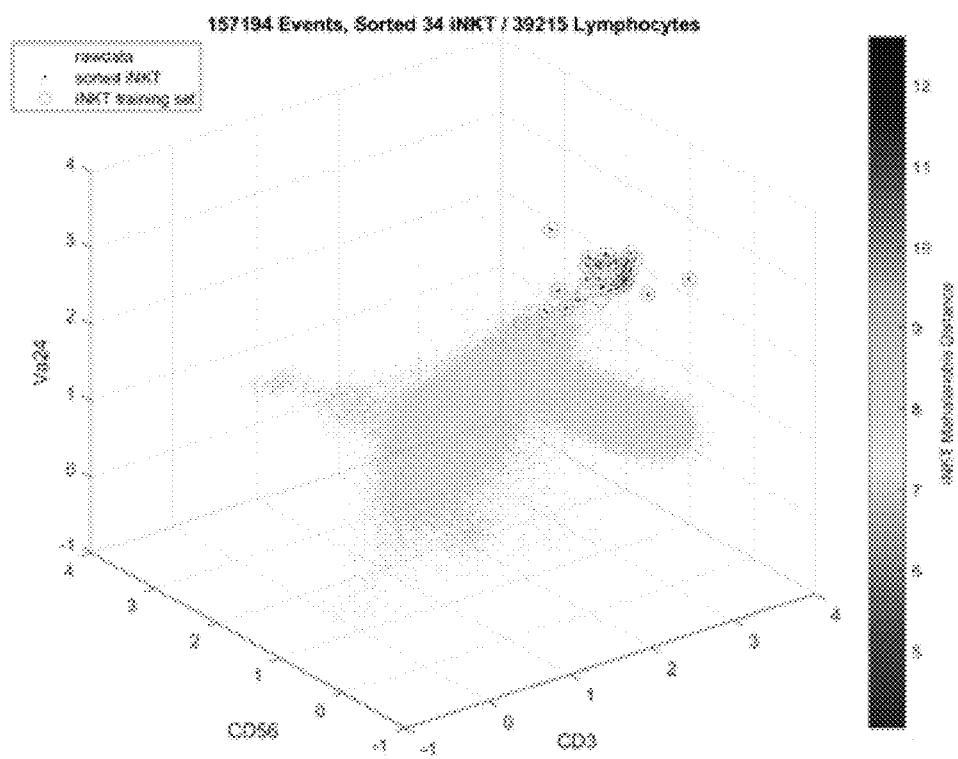
FIG. 9 is a triaxial scatter plot showing cells that were identified as invariant natural killer T (iNKT) cells in a training set and cells that were actually sorted into a pool of iNKTs in a collection vessel.

The system may also be self-correcting. For example, if a training set of particles presents false positives, the false positives may be revealed and corrected for when subsequent particles are analyzed or classified. In one case where Mahalanobis distance classification of single iNKT cells was used to identify iNKT cells in 7 immunofluorescence dimensions at once (CD45RA, CD38, CD57, CD3, Va24, CD11c, and CD314 markers), a training set included cells within the open circles depicted in FIG. 9. However, cells in those circles were not actually sorted based on a correction of the data that occurred as more events were gathered.

The features described may sort particles based on their membership to a target cluster. Mahalanobis distance may be used to measure a particle's distance to known clusters. The sort decision for particles may be based on which cluster the particle is closest to. For some samples, particles close to a contaminating cluster may be excluded or diverted to an alternate collection vessel. The criteria for determining closeness may be based on minimal probability of error. The probability may be defined using a configuration or specified as part of the experimental set up for a sample. Known clusters may be identified by training sets. A training set may include a subset of measurements of particles belonging to a cluster. The mean and covariance of a training set may be generated as a metric representation of a cluster. This metric may then serve as a factor in the Mahalanobis distance equation which may be evaluated using hardware capable of analyzing a measurement to generate a sort decision in time to direct a particle to a particular collection vessel.

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as specifically programmed event processing computers, wireless communication devices, or integrated circuit devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computing device, such as propagated signals or waves.

The program code may be executed by a specifically programmed graphics processor, which may include one or more processors, such as one or more digital signal processors (DSPs), configurable microprocessors, an application specific integrated circuits (ASICs), field programmable gate arrays (FPGAs), or other equivalent integrated or discrete logic circuitry. Such a graphics processor may be specially configured to perform any of the techniques described in this disclosure. A combination of computing devices, e.g., a combination of a DSP and a microprocessor, a plurality of microprocessors, one or more microprocessors in conjunction with a DSP core, or any other such configuration in at least partial data connectivity may implement one or more of the features describe. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a specialized graphic control card.

In some embodiments, the present disclosure provides integrated circuit devices programmed to perform one or more the computer-implemented methods described herein. In some instances, the subject integrated circuit devices are programmed to receive, from a particle analyzer, measurements for a first portion of particles associated with an experiment; generate a tree representing groups of related particles based at least in part on the measurements, wherein the tree includes at least three groups; generate a measure of relatedness between a first group and a second group of the tree based at least in part on the measurements; and configure the particle analyzer to classify a subsequent particle associated with the experiment with the first group, wherein the subsequent particle is not included in the first portion of particles.

In some embodiments, integrated circuit devices of interest include a field programmable gate array (FPGA). In other embodiments, integrated circuit devices include an application specific integrated circuit (ASIC). In yet other embodiments, integrated circuit devices include a complex programmable logic device (CPLD).

In certain embodiments, methods of the present disclosure also include sorting particles of the sample, such as cells of a biological sample. The term "sorting" is used herein in its conventional sense to refer to separating components (e.g., droplets containing cells, droplets containing non-cellular particles such as biological macromolecules) of a sample and in some instances, delivering the separated components to one or more sample collection containers. For example, methods may include sorting 2 or more components of the sample, such as 3 or more components, such as 4 or more components, such as 5 or more components, such as 10 or more components, such as 15 or more components and including sorting 25 or more components of the sample.

In some embodiments, methods for sorting components of sample include sorting particles (e.g., cells in a biological sample) with particle sorting module having deflector plates, such as described in U.S. Patent Publication No. 2017/0299493, filed on Mar. 28, 2017, the disclosure of which is incorporated herein by reference. In certain embodiments, cells of the sample are sorted using a sort decision module having a plurality of sort decision units, such as those described in U.S. Provisional Patent Application No. 62/803,264, filed on Feb. 8, 2019, the disclosure of which is incorporated herein by reference.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Various embodiments of the invention have been described. These and other embodiments are within the scope of the following claims.

Kits

Aspects of the present disclosure further include kits, where kits include one or more of the integrated circuit devices described herein. In some embodiments, kits may further include programming for the subject systems, such as in the form of a computer readable medium (e.g., flash drive, USB storage, compact disk, DVD, Blu-ray disk, etc.) or instructions for downloading the programming from an internet web protocol or cloud server. Kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject systems, methods and integrated circuits find use in a variety of applications where it is desirable to analyze and sort particle components in a sample in a fluid medium, such as a biological sample. In some embodiments, the systems and methods described herein find use in flow cytometry characterization of biological samples labelled with fluorescent tags. In other embodiments, the systems and methods find use in spectroscopy of emitted light. Embodiments of the present disclosure find use where it is desirable to provide a flow cytometer with improved cell sorting accuracy, enhanced particle collection, particle charging efficiency, more accurate particle charging and enhanced particle deflection during cell sorting.

Embodiments of the present disclosure also find use in applications where cells prepared from a biological sample may be desired for research, laboratory testing or for use in therapy. In some embodiments, the subject methods and devices may facilitate obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems may facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A computer-implemented method comprising:
under control of one or more processing devices,
receiving, from a particle analyzer, measurements for a first portion of particles associated with an experiment;
generating a tree representing groups of related particles based at least in part on the measurements, wherein the tree includes at least three groups;
generating a measure of relatedness between a first group and a second group of the tree based at least in part on the measurements; and
configuring the particle analyzer to classify a subsequent particle associated with the experiment with the first group, wherein the subsequent particle is not included in the first portion of particles.

2. The computer-implemented method of claim 1, further comprising:
receiving gate information identifying a range of measurements for classifying the subsequent particle, wherein the first group is defined by the gate information.

3. The computer-implemented method of claim 1, further comprising:

unsupervised learning, wherein unsupervised learning comprises identifying a range of measurements for classifying the subsequent particle without receiving gate information.

4. The computer-implemented method of claim 3, further comprising:
receiving gate information identifying a range of measurements for classifying the subsequent particle, wherein the first group is defined by the gate information;
determining that a difference between a result of the unsupervised learning, and the gate information, corresponds to a threshold; and
causing display of an alert identifying the difference.

5. The computer-implemented method of claim 1, further comprising:
generating the measure of relatedness between the first group and the second group based at least in part on a probability density function to characterize event distances between events included in the first group and the second group.

6. The computer-implemented method of claim 5, wherein the probability density function comprises a Euclidean distance function.

7. The computer-implemented method of claim 5, wherein the probability density function comprises a Mahalanobis distance function.

8. The computer-implemented method of claim 5, further comprising:
receiving an inclusion threshold for the first group, wherein the inclusion threshold identifies a first range of measurements for including an unclassified particle in the first group relative to the first group; and
receiving an exclusion threshold for the first group, wherein the exclusion threshold identifies a second range of measurements for excluding the unclassified particle from the first group relative to the second group;
wherein the subsequent particle is classified with the first group based at least in part on the inclusion threshold and the exclusion threshold.

9. The computer-implemented method of claim 1, further comprising:
generating a covariance matrix based at least in part on a likelihood of an association between the subsequent particle and each of the first group and the second group;
wherein configuring the particle analyzer includes adjusting a sorting circuit included in the particle analyzer based at least in part on the covariance matrix.

10. The computer-implemented method of claim 9, wherein the sorting circuit is a field programmable gate array.

11. The computer-implemented method of claim 1, wherein the measurements received from the particle analyzer comprise measurements of light emitted fluorescently by the first portion of particles.

12. The computer-implemented method of claim 11, wherein the light emitted fluorescently by the first portion of particles comprises light emitted fluorescently by antibodies bound to the first portion of particles.

13. The computer-implemented method claim 1, wherein generating the measure of relatedness is performed only for the first and second groups of the tree.

14. The computer-implemented method of claim 13, further comprising directing the subsequent particle to a collection vessel.

15. A system comprising:
one or more processing devices; and
a computer-readable storage medium comprising instructions that, when executed by the one or more processing devices, causes the system to,
receive, from a particle analyzer, measurements for a first portion of particles associated with an experiment;
generate a tree representing groups of related particles based at least in part on the measurements, wherein the tree includes at least three groups;
generate a measure of relatedness between a first group and a second group of the tree based at least in part on the measurements; and
configure the particle analyzer to classify a subsequent particle associated with the experiment with the first group, wherein the subsequent particle is not included in the first portion of particles.

16. A method of computational configuration of a particle analyzer according to any of the embodiments disclosed herein.

17. A computer-readable medium having stored thereon instructions which when executed perform any of the methods of claim 1.

18. An apparatus comprising a processor, wherein the processor is configured to perform any of the methods of claim 1.

19. The computer-implemented method of claim 1, wherein generating a tree representing groups of related particles comprises identifying clusters of related particles.

20. The computer-implemented method of claim 19, wherein the identified clusters of related particles comprise the groups of the tree.

* * * * *